(12) United States Patent
Suzumura et al.

(10) Patent No.: US 8,128,934 B2
(45) Date of Patent: Mar. 6, 2012

(54) METHOD FOR TREATMENT OR PREVENTION OF DISEASE ASSOCIATED WITH FUNCTIONAL DISORDER OF REGULATORY T CELL

(75) Inventors: Akio Suzumura, Aichi (JP); Jinyan Wang, Aichi (JP); Takashi Matsui, Kanagawa (JP); Sadatoshi Sakuma, Kanagawa (JP); Shin Miyakawa, Tokyo (JP); Masatoshi Fujiwara, Tokyo (JP); Yoshikazu Nakamura, Tokyo (JP)

(73) Assignees: Ribomic, Inc., Tokyo (JP); Cellmid Limited, Sydney (AU)

( * ) Notice: Subject to any disclaimer, the term of this patent is extended or adjusted under 35 U.S.C. 154(b) by 0 days.

(21) Appl. No.: 12/084,907

(22) PCT Filed: Nov. 14, 2006

(86) PCT No.: PCT/JP2006/322659
§ 371 (c)(1),
(2), (4) Date: Sep. 10, 2009

(87) PCT Pub. No.: WO2007/055378
PCT Pub. Date: May 18, 2007

(65) Prior Publication Data
US 2010/0092488 A1    Apr. 15, 2010

(30) Foreign Application Priority Data
Nov. 14, 2005 (JP) ................. 2005-329418

(51) Int. Cl.
*A61K 39/395* (2006.01)
*C07K 16/22* (2006.01)
(52) U.S. Cl. ................. 424/158.1; 530/387.1
(58) Field of Classification Search .......... None
See application file for complete search history.

(56) References Cited

U.S. PATENT DOCUMENTS
2003/0072739 A1* 4/2003 Takada et al. ................. 424/85.1

FOREIGN PATENT DOCUMENTS
| WO | 99/03493 | 1/1999 |
| WO | 2004/036221 | 4/2004 |
| WO | 2004/085642 | 10/2004 |
| WO | WO-2006/074179 | * 4/2006 |

OTHER PUBLICATIONS

Takei et al. Antisense oligdeoxynucleotide targeted to Midkine, a heparin-binding growth factor, suppresses tumorigenicity of mouse rectal carcinoma cells. Cancer Research 61, 2001, 8486-8491.*
Khan et al. Dendritic cells as targets for therapy in rheumatoid arthritis. Author manuscript; available in PubMedCentral, [online], Jun. 14, 2010, NIH Public Access, National Institutes of Health, Bethesda, MD [retrieved on Oct. 28, 2010]. Retrieved from the internet:URL:http://www.ncbi.nlm.nih.gov/pmc/articles/PMC2884969/pdf/nihms203323.pdf.*
U.S. Appl. No. 60/641,323, filed Jan. 4, 2005.*
Bowie et al. Deciphering the message in protein sequences: tolerance to amino acid substitutions. Science, (Mar. 16, 1990) 247 (4948) 1306-10.*
Ngo et al., in The Protein Folding Problem and Tertiary Structure Prediction, Merz and Le Grand (Eds), Aug. 1994, Springer Verlag, pp. 433 and 492-495.*
Baranzini SE. Systems-based medicine approaches to understand and treat complex diseases. The example of multiple sclerosis. Autoimmunity. Dec. 2006;39(8):651-62.*
Tsutsui, J. et al., A New Family of Heparin-binding Growth/Differentiation Factors: Increased Midkine Expression in Wilms' Tumor and Other Human Carcinomas, Cancer Research, vol. 53 (Mar. 15, 1993), pp. 1281-1285.
Kadomatsu, K. et al., Midkine induces the transformation of NIH3T3 cells, British Journal of Cancer, vol. 75, No. 3 (1997), pp. 354-359.
Horiba, M. et al., Neointima formation in a restenosis model is suppressed in midkine-deficient mice, The Journal of Clinical Investigation, vol. 105, No. 4 (Feb. 2000), pp. 489-495.
Sato, W. et al., Midkine Is Involved in Neutrophil Infiltration into the Tubulointerstitium in Ischemic Renal Injury, The Journal of Immunology, vol. 167 (2001), pp. 3463-3469.
Takada, T. et al., Midkine, a Retinoic Acid-Inducible Heparin-Binding Cytokine in Inflammatory Responses: Chemotactic Activity to Neutrophils and Association with Inflammatory Synovitis, J. Biochem, vol. 122, No. 2 (1997), pp. 453-458.
Maruyama, K. et al., Midkine, a Heparin-Binding Growth Factor, Is Fundamentally Involved in the Pathogenesis of Rheumatoid Arthritis, Arthritis & Rheumatism, vol. 50, No. 5 (May 2004), pp. 1420-1429.
Shevach, E., Regulatory T Cells in Autoimmunity, Annu. Rev. Immunol, vol. 18 (2000), pp. 423-449.
McGuirk, P. et al., Pathogen-specific regulatory T cells provoke a shift in the Th1/Th2 paradigm in immunity to infectious diseases, TRENDS in Immunology, vol. 23, No. 9 (Sep. 2002), pp. 450-455.
Roncarolo, M. et al., The role of different subsets of T regulatory cells in controlling autoimmunity, Current Opinion in Immunology, vol. 12 (2000), pp. 676-683.
Sakaguchi, S. et al., Organ-Specific Autoimmune Diseases Induced in Mice by Elimination of T Cell Subset, J. Exp. Med., vol. 161 (Jan. 1, 1985), pp. 72-87.

(Continued)

Primary Examiner — David Romeo
(74) Attorney, Agent, or Firm — Wenderoth, Lind & Ponack, LLP

(57) ABSTRACT

The inventors examined the role of MK in experimental autoimmune encephalomyelitis, which is a human model for multiple sclerosis. As a result, they discovered that MK has the effect of inhibiting regulatory T cells, and that the autoimmune mechanism induced by type 1 helper T cells can be suppressed by inhibiting MK expression or its activity, thereby increasing the number of regulatory T cells. Furthermore, it was found that diseases associated with the functional disorder of regulatory T cells can be treated with the administration of an inhibitor that inhibits MK expression or activity.

2 Claims, 7 Drawing Sheets

OTHER PUBLICATIONS

Itoh, M. et al., Thymus and Autoimmunity: Production of CD25+ CD4+ Naturally Anergic and Suppressive T Cells as a Key Function of the Thymus in Maintaining Immunologic Self-Tolerance, *The Journal of Immunology*, vol. 162 (1999), pp. 5317-5326.

Jonuleit, H. et al., Identification and Functional Characterization of Human CD4+ CD25+ T Cells with Regulatory Properties Isolated from Peripheral Blood, *J. Exp. Med.*, vol. 193, No. 11 (Jun. 4, 2001), pp. 1285-1294.

Levings, M. et al., Human CD25+ CD4+ T Regulatory Cells Suppress Naive and Memory T Cell Proliferation and Can Be Expanded In Vitro without Loss of Function, *J. Exp. Med.*, vol. 193, No. 11 (Jun. 4, 2001), pp. 1295-1301.

Dieckmann, D. et al., Ex Vivo Isolation and Characterization of CD4+ CD25+ T Cells with Regulatory Properties from Human Blood, *J. Exp. Med.*, vol. 193, No. 11 (Jun. 4, 2001), pp. 1303-1310.

Taams, L. et al., Human anergic/suppressive CD4+ CD25+ T cells: a highly differentiated and apoptosis-prone population, *Eur. J. Immunol.*, vol. 31 (2001), pp. 1122-1131.

Stephens, L. et al., *Human CD4+ CD25+ thymocytes and peripheral T cells have immune suppressive activity in vitro*, Eur. J. Immunol., vol. 31 (2001), pp. 1247-1254.

Baecher-Allan, C. et al., CD4+ CD25$^{high}$ Regulatory Cells in Human Peripheral Blood, *The Journal of Immunology*, vol. 167 (2001), pp. 1245-1253.

Groux, H. et al., A CD4+ T-cell subset inhibits antigen-specific T-cell responses and prevents colitis, *Nature*, vol. 389 (Oct. 16, 1997), pp. 737-742.

Jonuleit, H. et al., Induction of Interleukin 10-producing, Nonproliferating CD4+ T Cells with Regulatory Properties by Repetitive Stimulation with Allogeneic Immature Human Dendritic Cells, *J. Exp. Med.*, vol. 192, No. 9 (Nov. 6, 2000), pp. 1213-1222.

Sakaguchi, S., New perspectives of immune regulation mediated by Tcells, *Exp. Med.*, vol. 21, No. 16 (2003), pp. 2164-2168 (in the Japanese Language only).

Viglietta, V. et al., Loss of Functional Suppression by CD4+ CD25+ Regulatory T Cells in Patients with Multiple Sclerosis, *J. Exp. Med.*, vol. 199, No. 7 (Apr. 5, 2004), pp. 971-979.

Haas, J. et al., Reduced suppressive effect of CD4+ CD25$^{high}$ regulatory T cells on the T cell immune response against myelin oligodendrocyte glycoprotein in patients with multiple sclerosis, *Eur. J. Immunol.*, vol. 35 (2005), pp. 3343-3352.

Huan, J. et al., Decreased FOXP3 Levels in Multiple Sclerosis Patients, *Journal of Neuroscience Research*, vol. 81 (2005), pp. 45-52.

Furtado, C. et al., Regulatory T cells in spontaneous autoimmune encephalomyelitis, *Immunological Reviews*, vol. 182 (2001), pp. 122-134.

Hori, S. et al., Specificity requirements for selection and effector functions of CD25+4+ regulatory T cells in anti-myelin basic protein T cell receptor transgenic mice, *Proc. Natl. Acad. Sci. USA*, vol. 99, No. 12 (Jun. 11, 2002), pp. 8213-8218.

Kohm, A. et al., Cutting Edge: CD4+ CD25+ Regulatory T Cells Suppress Antigen-Specific Autoreactive Immune Responses and Central Nervous System Inflammation During Active Experimental Autoimmune Encephalomyelitis, *The Journal of Immunology*, vol. 169 (2002), pp. 4712-4716.

Balandina, A. et al., Functional defect of regulatory CD4+ CD25+ T cells in the thymus of patients with autoimmune myasthenia gravis, *Blood*, vol. 105, No. 2 (Jan. 15, 2005), pp. 735-741.

Coombes, J. et al., Regulatory T cells and intestinal homeostasis, *Immunological Reviews*, vol. 204 (2005), pp. 184-194.

Read, S. et al., Cytotoxic T Lymphocyte-associated Antigen 4 Plays an Essential Role in the Function of CD25+ CD4+ Regulatory Cells that Control Intestinal Inflammation, *J. Exp. Med.*, vol. 192, No. 2 (Jul. 17, 2000), pp. 295-302.

Alvarado-Sanchez, B. et al., Regulatory T cells in patients with systemic lupus erythematosus, *Journal of Autoimmunity*, vol. 27 (2006), pp. 110-118.

Green, E. et al., CD4+ CD25+ T regulatory cells control anti-islet CD8+ T cells through TGF-$\beta$-TGF-$\beta$ receptor interactions in type 1 diabetes, *Proc. Natl. Acad. Sci. USA*, vol. 100, No. 19 (Sep. 16, 2003), pp. 10878-10883.

Dai, Z. et al., CD4+ CD25+ regulatory T cells suppress allograft rejection mediated by memory CD8+ T cells via a CD30-dependent mechanism, *The Journal of Clinical Investigation*, vol. 113, No. 2 (Jan. 2004), pp. 310-317.

Wei, W. et al., Anti-tumor immunity and autoimmunity: a balancing act of regulatory T cells, *Cancer Immunol Immunother*, vol. 53 (2004), pp. 73-78.

Frey, O. et al., The role of regulatory T cells in antigen-induced arthritis: aggravation of arthritis after depletion and amelioration after transfer of CD4+ CD25+ T cells, *Arthritis Res. Ther.*, vol. 7, No. 2 (2005), pp. R291-R301.

Lan, R. et al., Regulatory T cells: Development, function and role in autoimmunity, *Autoimmunity Reviews*, vol. 4 (2005), pp. 351-363.

Liu X et al. Basic FGF and FGF receptor 1 are expressed in microglia during experimental autoimmune encephalomyelitis: temporally distinct expression of midline and pleiotrophin. Glia. Dec. 1998;24(4):390-7.

MIR Preclinical Services 2010, *MIR Preclinical Services: Models of Arthritis and Inflammation.* http://www.molecularimaging.com/inflammation_arthritis.htm>. [Jul. 29, 2010].

Sakaguchi, S., New perspectives of immune regulation mediated by T cells, *Exp. Med.*, vol. 21, No. 16 (2003), pp. 2164-2168 (English Abstract).

* cited by examiner

[Fig.1]
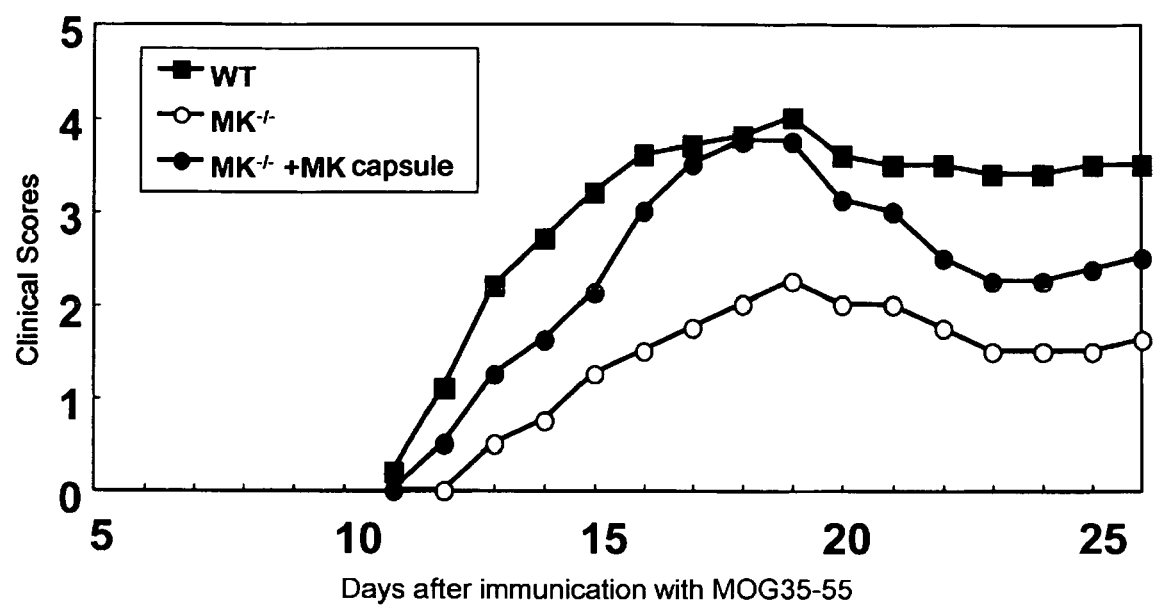

[Fig.2]
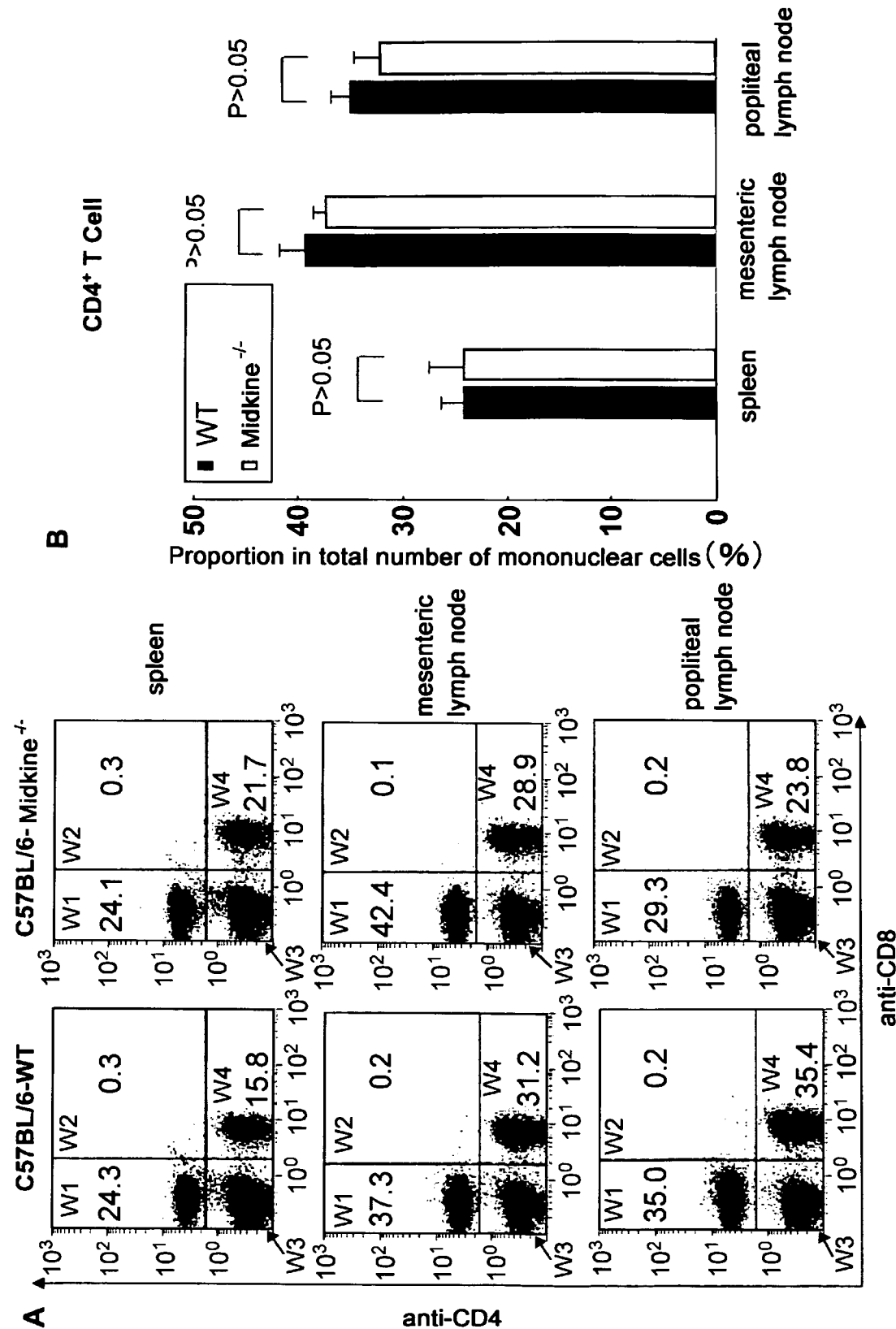

[Fig.3]
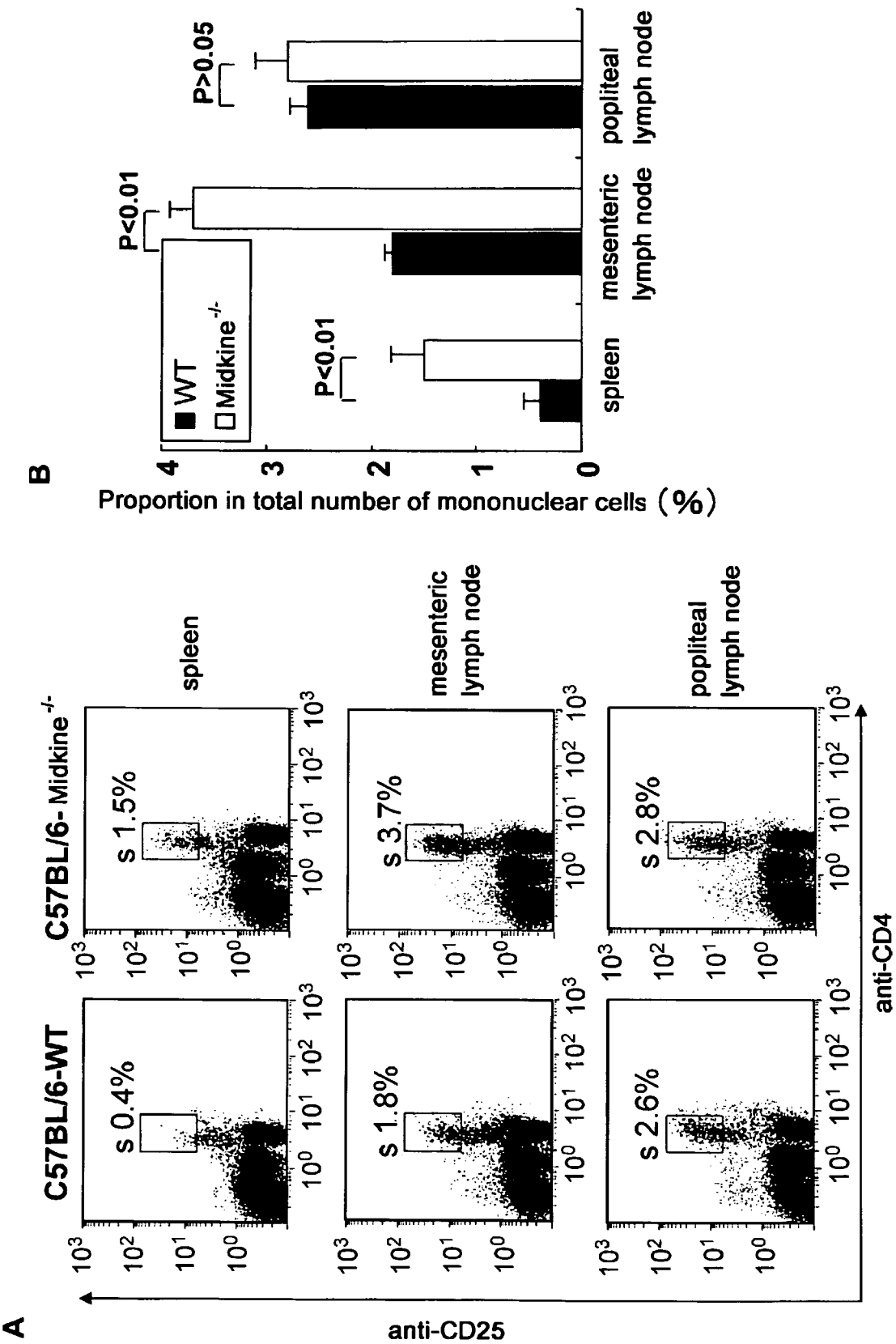

[Fig.4]
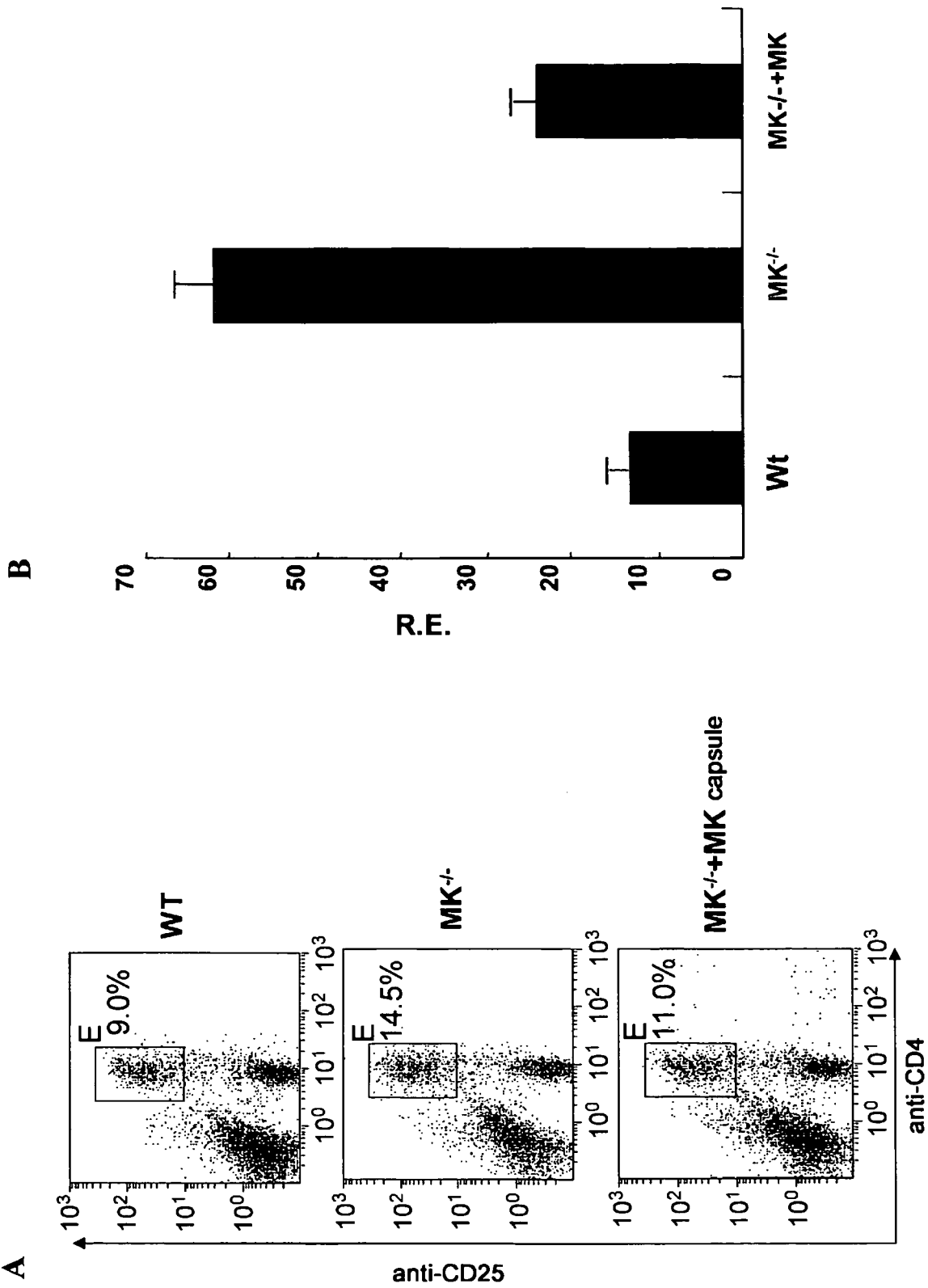

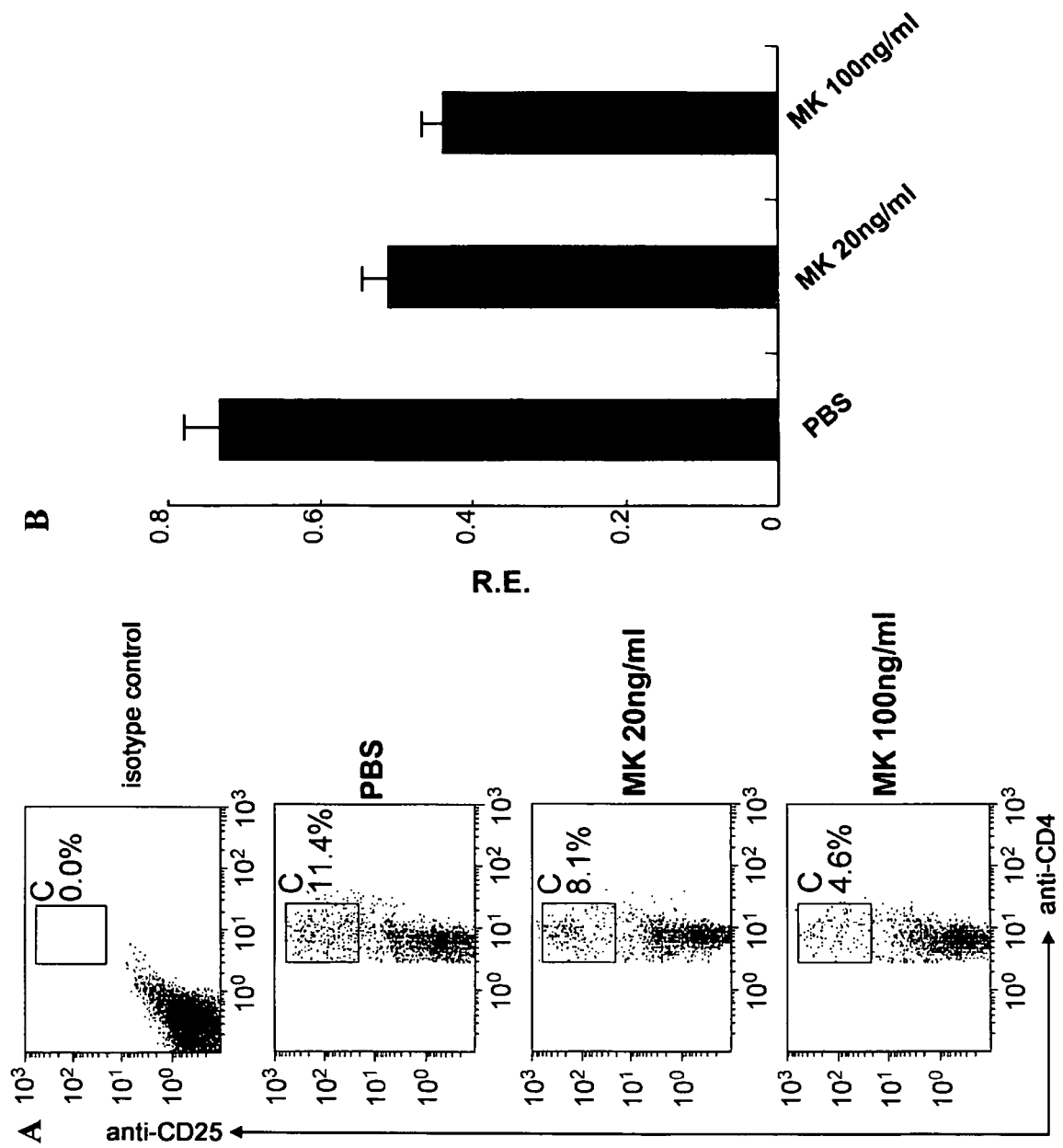
[Fig.5]

[Fig.6]
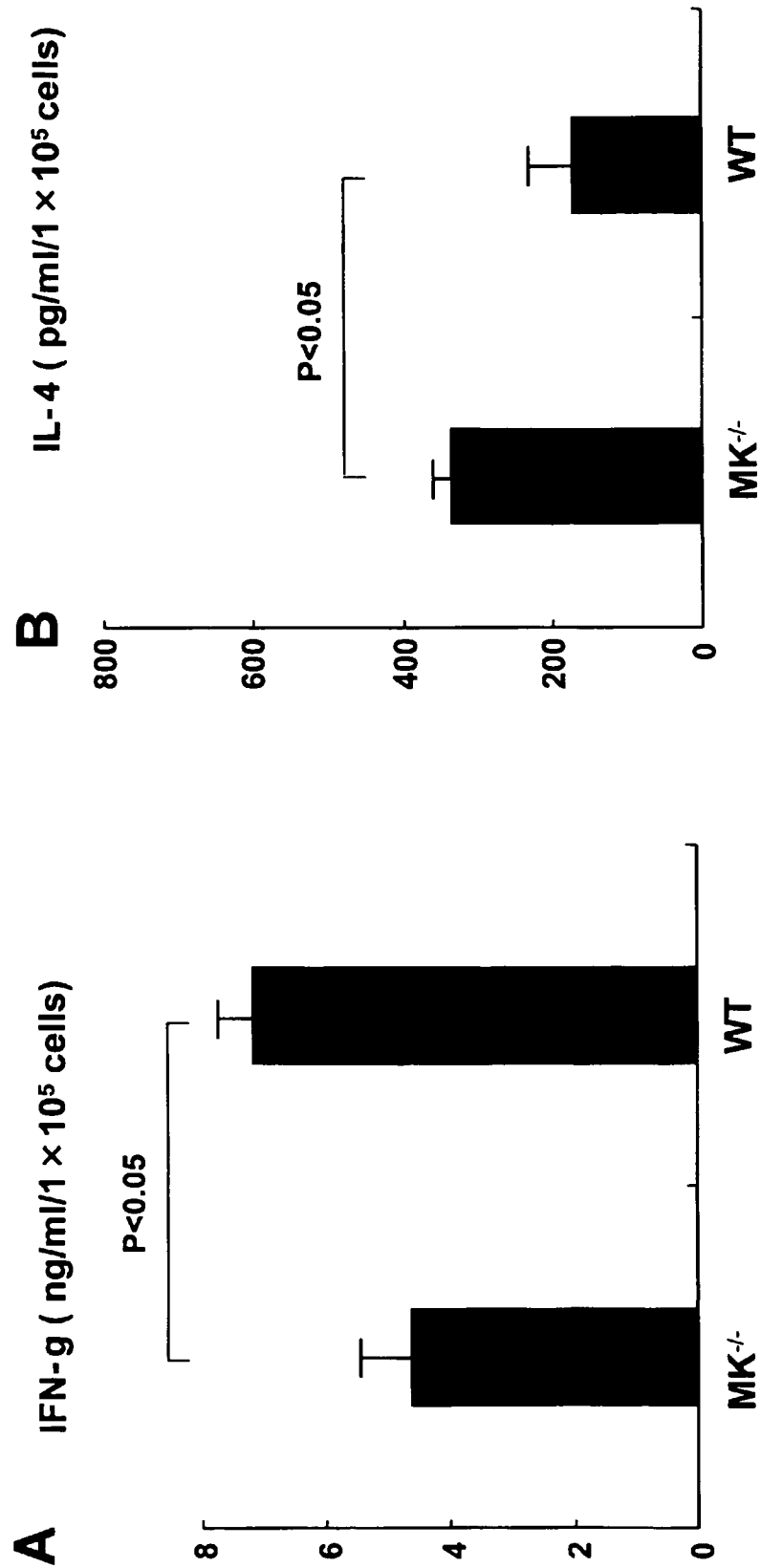

[Fig.7]
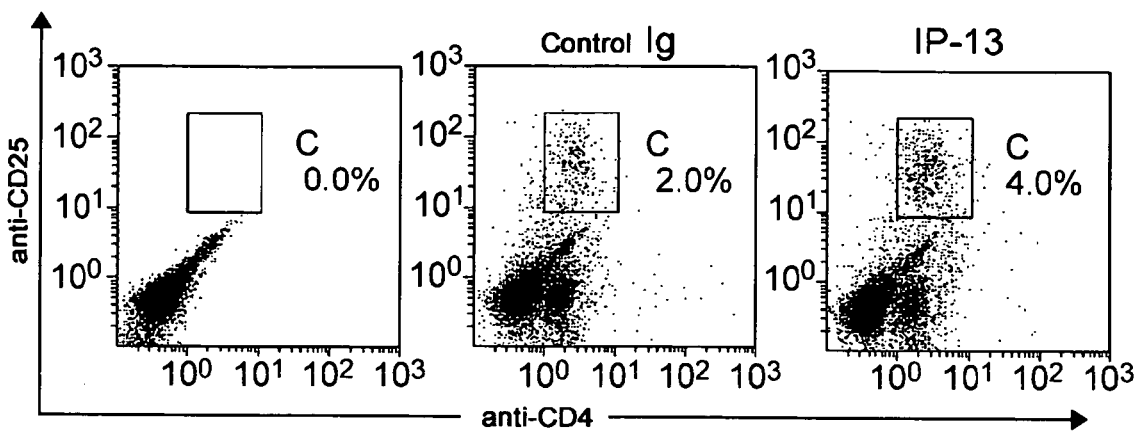
[Fig.8]
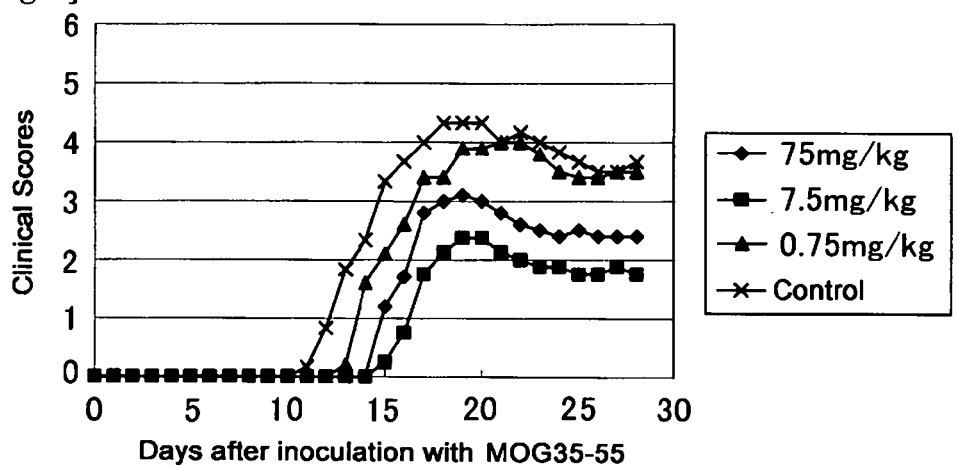
[Fig.9]
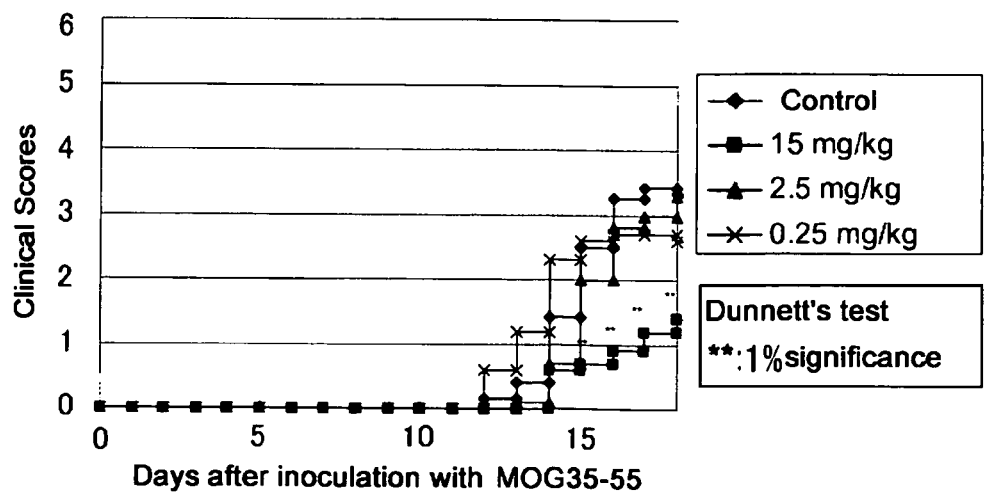

METHOD FOR TREATMENT OR PREVENTION OF DISEASE ASSOCIATED WITH FUNCTIONAL DISORDER OF REGULATORY T CELL

This application is a U.S. national stage of International Application No. PCT/JP2006/322659 filed Nov. 14, 2006.

FIELD OF THE INVENTION

The present invention pertains to an expansive agent for regulatory T cell population and/or a therapeutic agent for diseases associated with the functional disorder of regulatory T cells comprising a midkine inhibitor as its active ingredient. It also pertains to a method for increasing number of regulatory T cells by inhibiting midkine, a method for treatment or prevention of disease associated with the functional disorder of regulatory T cells comprising the administration of a midkine inhibitor, and/or a method for screening a drug composition for the treatment or prevention of disease associated with the functional disorder of regulatory T cells. Furthermore, it pertains to a method for examining disease associated with the functional disorder of regulatory T cells that includes a process of assaying the midkine expression level.

RELATED ART

Midkine (hereinafter may be abbreviated as MK) is a member of the heparin-binding growth factor family, and is a non-glycosylated protein found to be the product of a gene responsive to retinoic acid. Its receptor is believed to be a complex consisting of receptor-type protein tyrosine phosphatase zeta, LRP (low-density lipoprotein receptor-related protein), ALK (anaplastic leukemia kinase), integrin and syndecan. MK is known to have cell migratory and angiogenic activity, as well as diverse bioactivity in canceration and inflammation; there have also been reports of overexpression of MK in the numerous cancerous tissues such as gastric cancer, colon cancer and breast cancer (non-patent references 1 and 2). Meanwhile, there have also been reports of intimal disorders and ischemic renal disease in MK-deficient mice (non-patent references 3 and 4).

In recent years, it has been indicated that MK may cause inflammatory cell migration and osteoclast differentiation, and may playing an important role in rheumatic diseases (non-patent references 5 and 6); however, the role of MK in immunological competence remains unknown.

T cells are one of the group of cells that play a central role in the immune system that defends the body against various pathogens. T cells can be roughly divided into CD4-positive helper T cells and CD8-positive cytopathic T cells. CD4-positive helper T cells can be classified in accordance with their cytokine-production pattern in specific stage of mature differentiation following antigen stimulation into such as Th1 cells and Th2 cells, which primarily produce IFN-gamma and IL-4, respectively. In general, Th1 cells and Th2 cells relate to biological defense, in the form of cell-mediated immunity and in the form of antibody-mediated immunity, respectively. The immune response relates to the elimination of pathogens and the acquirement of resistance to infection under a delicate balance through the functions of T cells of different characteristics. Normally, a healthy immune response mechanism eliminates foreign non-self antigens. At the same time, immunological tolerance keeps the elimination mechanism from functioning against autoantigens which are component within the body. As mentioned above, the body distinguishes between self and non-self antigens, and possesses a mechanism that eliminates only non-self antigens. In autoimmune diseases, this immunological homeostasis function is lost and the resultant hyperimmune response to self antigen causes the diseases.

The mechanisms by which various immunological tolerances are derived at the T cell level are known. One is the mechanism of eliminating autoreactive T cell clones in the thymus, known as central tolerance. The central tolerance comprises positive selection, through which only those cells that recognize Major Histocompatibility Complex are able to survive; and negative selection, through which cells that react strongly to autoantigens presented by thymocytes are eliminated. Another one is extrathymic control of autoreactive T cells through a mechanism known as peripheral tolerance. Peripheral tolerance mechanisms include inducement of cell death or nonresponsiveness to autoantigens, as well as active control by regulatory T cells (non-patent reference 7).

The regulatory T cells are new concept that has been proposed in recent years, and is defined to have inhibitory action against other T cells (non-patent reference 8). The immune response comprises a delicate balancing act, for example, Th1 cells and Th2 cells work antagonistically each other against their respective immune responses, and one works as the regulatory T cell to the other. There remains much room for argument about the verification of the existence of a cell population of regulatory T cells and the analysis of their nature. These regulatory T cells are studied in vitro or in vivo as cells having the function of inhibiting or adjusting specific immune responses, and have been reported as various cell populations by type of cell surface marker or cytokine produced, or by mechanism of inhibition or adjustment (non-patent reference 9).

Among these regulatory T cells, the most studied cell population is the CD4-positive, CD25-positive regulatory T cell population. Removal of CD25-positive, RT6.1-positive, CD5-positive, CD45RB-positive, CD45RC-positive, etc. cells from CD4-positive splenocytes of normal mice and rats, and the infusion of remaining T cells into T cell- and B cell-deficient SCID mice and rats induce organ-specific autoimmune diseases such as thyroiditis, gastritis, insulin-dependent autoimmune diabetes and colitis (non-patent references 10 and 11). Furthermore, insertion of CD25-negative CD4-positive cells into nude mice give rise to organ-specific autoimmune diseases, and insertion of peripheral CD4-positive, CD25-positive cells together with CD25-positive, CD4-positive, CD8-negative thymocytes suppresses the development of disease. These studies have contributed to the understanding that CD4-positive, CD25-positive regulatory T cells play an extremely important role in maintaining autotolerance.

It is known that similar CD4-positive, CD25-positive regulatory T cells are present in humans as well (non-patent references 12, 13, 14, 15, 16 and 17). CD4-positive, CD25-positive T cells isolated from human peripheral blood express CD45RO-positive memory T cell markers, and their expression level of activation markers such as HLA-DR is higher than that of CD4-positive, CD25-negative T cells. Furthermore, CTLA-4 is expressed steadily in the CD4-positive, CD25-positive cells and the expression level of CTLA-4 increases by stimulation. CD4-positive, CD25-positive T cells do not promote DNA synthesis or cytokine production after stimulation such as anti-CD3 antibody stimulation, stimulation by anti-CD3 and anti-CD28 antibodies or stimulation by allogeneic mature dendritic cells which indicates nonresponsiveness of the cells to antigenic stimulation. The addition of cytokines such as IL-2, IL-4 and IL-15 to the stimulation by anti-CD3 and anti-CD28 antibodies increases the DNA synthesize ability of CD4-positive, CD25-positive T cells, but does not change that ability of CD4-positive, CD25-negative T cells. The stimulation of CD4-positive, CD25-negative T cells by anti-CD3 antibodies or allogeneic mature dendritic cells in the presence of CD4-positive, CD25-positive T cells showed more anti-increasing in number effect dependent on the number of CD4-positive, CD25-positive T cells than the same stimulation in the absence of CD4-positive, CD25-positive T cells. There have been reports that while CD4-positive, CD25-positive T cells were able to produce inhibitory cytokines such as IL-10 and TGF beta1, the anti-increasing in number effect against CD4-positive, CD25-negative T cells is not lost by the neutralizing antibodies against these cytokines, and that the anti-increasing in number effect required direct intercellular contact between CD4-positive, CD25-negative T cells and CD4-positive, CD25-positive T cells. As mentioned above, there have been reports on the existence of CD4-positive, CD25-positive regulatory T cells in humans, and their properties has been investigated, but there has yet to be a fully detailed explanation of the mechanisms of their differentiation and inhibition.

There have also been reports regarding regulatory T cells that are induced by repeated stimulation by allogeneic antibodies and/or allogeneic immature dendritic cells in the presence of IL-10 in mice and humans (non-patent references 18 and 19). Unlike Th1 and Th2 cells, these cells are called Tr1 cells and characterized by high production of IL-10; moderate production of TGF-beta1, IFN-gamma and IL-5; low production of IL-2; and no production of IL-4. Similar to CD4-positive, CD25-positive regulatory T cells, Tr1 cells are nonresponsive, while the mechanism to suppress T cells can be partially explained by the IL-10 and TGF-beta1 produced by the Tr1 cells. However, it is not all clear whether Tr1 cells and CD4-positive, CD25-positive regulatory T cells are completely different subsets of T cells, or are different differentiation/activation stages of the same cell population.

In the X-linked recessive inheritance disorder called IPEX, there is a high incidence of inflammatory colitis, allergies and organ-specific autoimmune diseases such as insulin-dependent diabetes and thyroiditis. The gene which causes this disorder is believed to be FOXP3. It is known that FOXP3 is selectively expressed in CD4-positive, CD25-positive regulatory T cells. Also, it appears that the expression of FOX3 gene in other T cells can functionally convert the T cells into CD4-positive, CD25-positive regulatory T cells. Furthermore, mice with abnormal FOXP3 gene developed serious autoimmune disorders, and the disorders were prevented by the infusion of CD4-positive, CD25-positive regulatory T cells prepared from normal mice (non-patent reference 20).

It is known that CD4-positive, CD25-positive regulatory T cells are deeply correlated with multiple sclerosis. Patients with relapsing-remitting multiple sclerosis (RRMS) had a notably reduced amount of CD4-positive, CD25-positive regulatory T cells (non-patent references 21, 22 and 23). Also, in studies using the experimental autoimmune encephalomyelitis (EAE) mouse model, which is considered to be a model of multiple sclerosis, it has been reported that CD4-positive, CD25-positive regulatory T cells inhibit development of EAE as well as the increase in number of T cells and the production of IFN-gamma against myelin oligodendrocyte glycoprotein (MOG) (non-patent references 24, 25 and 26). Myasthenia gravis (MG) is believed to be a CD4-positive T cell-dependent autoimmune disease, and it has been reported that patients with myasthenia gravis have functional abnormality of CD4-positive, CD25-positive regulatory T cells and reduced FOXP3 expression (non-patent reference 27). CD4-positive, CD25-positive regulatory T cells are also correlated with inflammatory bowel disease (IBD) and Crohn's disease. Infusion of CD4-positive, CD45RB$^{high}$ T cells into immunodeficient mice causes Th1 cell-induced colitis. On the other hand, concomitant infusion of CD4-positive, CD25-positive regulatory T cells with CD4-positive, CD45RB$^{high}$ T cells does not cause colitis (non-patent references 28 and 29). There have also been numerous studies on the correlation of CD4-positive, CD25-positive regulatory T cells with rheumatoid arthritis (RA) and systemic lupus erythematosus (SLE). It has been reported that from analysis of regulatory T cells in the peripheral blood of 23 subjects with SLE (19 active and 4 inactive), 15 subjects with RA and 27 healthy subjects, the number of CD4-positive, CD25-positive regulatory T cells showed no difference among the SLE subjects, RA subjects and healthy subjects, but the suppressive function of the cells was greatly reduced among the SLE subjects and RA subjects compared to the healthy subjects (non-patent reference 30). It is also known that CD4-positive, CD25-positive regulatory T cells are correlated with type I diabetes (non-patent reference 31), transplant rejection reaction (non-patent reference 32) and cancer (non-patent reference 33).

CD4-positive, CD25-positive regulatory T cells are a rare cell population, accounting for only 5 to 10% of CD4-positive T cells in peripheral blood, and are nonresponsive to activation stimuli. Cell increase can be promoted by adding cytokines such as IL-2, IL-4 and IL-15 to the stimulation by anti-CD3 antibodies and anti-CD28 antibodies. It is anticipated that increase of the number of CD4-positive, CD25-positive regulatory T cells will be applied to the treatment of autoimmune diseases, transplants and allergies.

Multiple sclerosis (hereinafter may be abbreviated as MS) is an autoimmune disease that causes inflammatory demyelination in the central nervous system. It has been assumed that various immune cells play a role in the disease, but the true nature of the disease has yet to be understood. In recent years, it has been indicated that regulatory T cells (CD4-positive, CD25-positive, FOXP3-positive T cells) inhibitory regulate MS disease condition. CD4-positive, CD25-positive regulatory T cells regulate autoimmune expression by maintaining immunological tolerance. Thus, it is believed that the functional abnormality of these cells contributes to the pathogenesis of various autoimmune diseases, but the details of this mechanism remain to be elucidated.

Below are references for related art to the invention of the present application.

Non-patent reference 1: Tsutsui, J., et al., 1993. Cancer Res., 53: 1281-1285

Non-patent reference 2: Kadomatsu, K., et al., 1997. Brit. J. Cancer, 75:354-359

Non-patent reference 3: Horiba, M., et al., 2000. J. Clin. Invest., 105: 489-495

Non-patent reference 4: Sato, W., et al., 2001. J. Immunol., 167:3463-3469

Non-patent reference 5: Takada, T., et al., 1997. J. Biochem, 122(2):453-458

Non-patent reference 6: Maruyama, K., et al., 2004. Arthritis Rheum., 50(5): 1420-1429

Non-patent reference 7: Shevach, E. M. 2000. Annu. Rev. Immunol. 18:423-449

Non-patent reference 8: McGuirk P., et al., 2002. Trends in Immuno. 23:450-455

Non-patent reference 9: Roncarolo, M. G., and M. K. Levings. 2000. Curr. Opinion. Immunol. 12:676-683

Non-patent reference 10: Sakaguchi, S., et al., 1985. J. Exp. Med. 161:72

Non-patent reference 11: Itoh, M., et al., 1999. J. Immunol. 162:5317-5326

Non-patent reference 12: Jonuleit, H. et al., 2001. J. Exp. Med. 193:1285-1294

Non-patent reference 13: Levings, M. K. et al., 2001. J. Exp. Med. 193: 1295-1301

Non-patent reference 14: Dieckmann, D. et al., 2001. J. Exp. Med. 193:1303-1310

Non-patent reference 15: Taama, L. S. et al., 2001. Eur. J. Immunol. 31:1122-1131

Non-patent reference 16: Stephens, L. A. et al., 2001. Eur. J. Immunol. 31:1247-1245

Non-patent reference 17: Baecher-Allan, C. et al., 2001. J. Immunol. 167:1245-1253

Non-patent reference 18: Groux, H. et al., 1997. Nature 389:737-742

Non-patent reference 19: Jonuliet, H. et al., 2000. J. Exp. Med. 192:1213-1222

Non-patent reference 20: Sakaguchi, S, 2003, Exp. Med. 21: 2164-2168.

Non-patent reference 21: Viglietta et al., 2004. J. Exp. Med. 199:971-979

Non-patent reference 22: Haas et al., 2005. Eur. J. Immunol. 35:3343-3352

Non-patent reference 23: Huan et al., 2005. J. Neurosci. Res. 81:45-52

Non-patent reference 24: Furtado et al., 2001. Immunol. Rev. 182:122-134

Non-patent reference 25: Hori et al., 2002. Proc. Natl. Acad. Sci. USA 99:8213-8218

Non-patent reference 26: Kohm et al., 2002. J. Immunol. 169: 4712-4716

Non-patent reference 27: Balandia et al., 2005. Blood 105: 735-741

Non-patent reference 28: Coombes et al., 2005. Immunol. Rev. 204: 184-194

Non-patent reference 29: Read et al., 2000. J. Exp. Med. 192: 295-302

Non-patent reference 30: Alvarado-Sanchez et al., 2006. J. Autoimmunity 27: 110-118

Non-patent reference 31: Green et al., 2003. Proc. Natl. Acad. Sci. USA 100: 10878-10883

Non-patent reference 32: Dai et al., 2004. J. Clin. Invest. 113:310-317

Non-patent reference 33: Wei et al., 2004. Cancer Immunol. Immunother. 53: 73-78

DISCLOSURE OF THE INVENTION

Problems to be Solved by the Invention

The present invention was developed in consideration of the situation described above, and the aim of the invention is to provide a an expansive agent for regulatory T cell population comprising an MK inhibitor as an active ingredient. The other aims of the invention is to provide a therapeutic agent for diseases associated with the functional disorder of regulatory T cells comprising an MK inhibitor as its active ingredient. Furthermore, the present invention may provide a method for screening a drug composition that inhibits MK expression or activity for the treatment or prevention of disease associated with the functional disorder of regulatory T cells. In addition, the present invention may provide a method for examining disease associated with the functional disorder of regulatory T cells that includes a step of detecting the MK expression level.

Means to Solve the Problems

The inventors discovered that the number of CD4-positive, CD25-positive regulatory T cells had increased in MK-deficient mice, and that administration of MK reduced the number of CD4-positive, CD25-positive regulatory T cells. In addition, the inventors achieved the following results from their study of experimental autoimmune encephalomyelitis (hereinafter may be abbreviated as EAE), which is a model of multiple sclerosis.

First, inducement of EAE to the MK-deficient mice showed mitigation of clinical symptoms (FIG. 1). This effect was eliminated by the treatment with MK (FIG. 1).

Next, the dynamics of CD4-positive, CD25-positive regulatory T cells in said EAE model animals were examined to investigate the role of MK in EAE expression and CD4-positive, CD25-positive regulatory T cell function. Since EAE is a disease induced by type 1 helper T cells (Th1), the Th1/Th2 balance in MK-deficient mice was also investigated to examine the effect of MK on the Th1/Th2 balance.

The results of these studies indicated that changes in the CD4-positive cells which induce the disease were not responsible for the mitigation of clinical symptoms in these model animals (FIGS. 2a, 2b), but an increase in the number of CD4-positive, CD25-positive regulatory T cells were responsible for the mitigation (FIGS. 3a, 3b, 4a, 4b). In addition, EAE inducement in MK-deficient mice led an increased number of CD4-positive, CD25-positive cells compared to the EAE inducement in wild type mice, and administration of MK decreased the number of CD4-positive, CD25-positive cells (FIGS. 5a, 5b). Furthermore, an increase in the number of these CD4-positive, CD25-positive regulatory T cells inhibited type 1 helper T cells, which induce cell-mediated immunity (FIGS. 6a, 6b).

Next, the effect of treatment with anti-MK antibodies, which is one of the MK inhibitor, on CD4-positive, CD25-positive regulatory T cell dynamics in EAE model mice was analyzed. The results indicated that treatment with the MK inhibitor mitigated clinical symptoms (FIG. 8). Specifically, there was delayed onset and reduced severity of the disease in the mice immunized with $MOG_{35-55}$ and then had been treated with anti-MK antibodies (FIG. 8).

Furthermore, the EAE model mice were treated with an anti-MK aptamer, which is one of MK inhibitor, and the clinical symptoms were observed. The results indicated mitigation of clinical symptoms similar to that of the treatment with anti-MK antibodies (FIG. 9).

In other words, the inventors discovered that MK has the effect of inhibiting the increase in number of regulatory T cells and function of regulatory T cells, and that inhibition of MK expression or activity can eliminate the MK's inhibitory effect to the increase and function of regulatory T cells, as overviewed above, the inventors achieved the present invention.

More specifically, the present invention provides (1) through (20) below.

(1) An expansive agent for regulatory T cell population comprising a MK inhibitor as an active ingredient.

(2) An expansive agent for regulatory T cell population as set forth in (1), wherein the MK inhibitor is selected from the group consisting of anti-MK antibodies, aptamers against MK, antisense RNA and dsRNA.

(3) An expansive agent for regulatory T cell population as set forth in (1), wherein the MK inhibitor is either anti-MK antibodies or aptamers against MK.

(4) A therapeutic or preventive agent for diseases associated with the functional disorder of regulatory T cells comprising a MK inhibitor as an active ingredient.

(5) A therapeutic or preventive agent for diseases associated with the functional disorder of regulatory T cells as set forth in (4), wherein the MK inhibitor is selected from the group consisting of anti-MK antibodies, aptamers against MK, antisense RNA and dsRNA.

(6) A therapeutic or preventive agent for diseases associated with the functional disorder of regulatory T cells as set forth in (4), wherein the MK inhibitor is either anti-MK antibodies or aptamers against MK.

(7) A therapeutic or preventive agent as set forth in one of (4) through (6), wherein the disease associated with the functional disorder of regulatory T cells is an autoimmune disease, allergic disease, chronic transplant rejection, thyroid abnormality, inflammatory colitis, type 1 diabetes, multiple sclerosis, myasthenia gravis, rheumatoid arthritis, systemic lupus erythematosus, or amyotrophic lateral sclerosis.

(8) A therapeutic agent as set forth in one of (4) through (6), wherein the disease associated with the functional disorder of regulatory T cells is multiple sclerosis.

(9) A method for increasing the number of regulatory T cells comprising of inhibition of MK.

(10) A method for increasing the number of regulatory T cells comprising of administration of a MK inhibitor.

(11) A use of an MK inhibitor in the manufacture of a an expansive agent for regulatory T cell population.

(12) A method for the treatment or prevention of disease associated with the functional disorder of regulatory T cells comprising of inhibition of MK.

(13) A method for the treatment or prevention of disease associated with the functional disorder of regulatory T cells comprising of administration of a MK inhibitor.

(14) A use of a MK inhibitor in the manufacture of a therapeutic or preventive agent for disease associated with the functional disorder of regulatory T cells.

(15) A method for screening a medicament for the treatment or prevention of disease associated with the functional disorder of regulatory T cells by binding to the expressed MK, comprising:
  (a) a step of contacting a test compound to MK;
  (b) a step of detecting said binding between MK and a test compound; and
  (c) a step of selecting the compound which binds to MK.

(16) A method for screening a drug composition for the treatment or prevention of disease associated with the functional disorder of regulatory T cells by inhibiting MK expression, comprising:
  (a) a step of contacting a test compound to cells expressing MK gene;
  (b) a step of assaying the MK expression level of said cells; and
  (c) a step of selecting the compound which reduces the MK expression level compared to that level of cells to which the test compound was not contacted.

(17) A method for screening a medicament for the treatment or prevention of disease associated with the functional disorder of regulatory T cells by inhibiting MK expression, comprising:
  (a) a step of providing cells having DNA in which a reporter gene is functionally located downstream from the promoter region of the DNA encoding MK, or an extract thereof;
  (b) a step of contacting a test compound to said cells or said cell extract;
  (c) a step of assaying the expression level of said reporter gene in said cells or said cell extract; and
  (d) a step of selecting the compound which reduces the expression level of said reporter gene compared to that expression level of cells or cell extract to which the test compound was not contacted.

(18) A method for screening a medicament for the treatment or prevention of diseases associated with the functional disorder of regulatory T cells by inhibiting MK activity, comprising:
  (a) a step of contacting a test compound to cells that express MK;
  (b) a step of assaying MK activity in said cells; and
  (c) a step of selecting the compound which reduces the above-mentioned activity compared to the MK activity of cells that express MK to which the test compound was not contacted.

(19) A method of diagnosing diseases associated with the functional disorder of regulatory T cells comprising a step of assaying the MK expression level.

(20) A diagnostic agent for diseases associated with the functional disorder of regulatory T cells comprising a substance that binds to Midkine.

BRIEF EXPLANATION OF DRAWINGS

[FIG. 1] The figure indicates the results of observation of clinical symptoms in wild-type mice (C57BL-6), MK-deficient mice and MK-deficient mice treated with MK, in which experimental autoimmune encephalomyelitis had been induced. The mean values for all animals to day 25 following immunization are shown. A curve is drawn in accordance with the Kaplan-Meier method.

[FIG. 2] The figure indicates the proportion of CD4-positive T cells in the peripheral lymph nodes of wild-type mice (C57BL-6) and MK-deficient mice following immunization with $MOG_{35-55}$. Figure A indicates the in vivo ratio of CD4-positive and CD8-positive cells in the spleen, mesenteric lymph nodes and popliteal lymph nodes of wild-type mice and MK-deficient mice. Figure B indicates the proportion of CD4-positive T cells among all mononuclear cells in the three sites mentioned above. The values are expressed as mean±SEM. The p value was calculated in accordance with the student t-test.

[FIG. 3] The figure indicates the proportion of CD4-positive, CD25-positive T cells in the peripheral lymph nodes of wild-type mice (C57BL-6) and MK-deficient mice following immunization with $MOG_{35-55}$. Figure A indicates the cytofluorescence characteristic of in vivo CD4-positive, CD25-positive T cells in the spleen, mesenteric lymph nodes and popliteal lymph nodes of wild-type mice and MK-deficient mice. Figure B indicates the proportion of CD4-positive, CD25-positive T cells among all mononuclear cells in the three sites mentioned above. The values are expressed as mean±SEM. The p value is calculated in accordance with the student t-test.

[FIG. 4] The figure indicates the dynamics of CD4-positive, CD25-positive regulatory T cells in experimental autoimmune encephalomyelitis model animals. Figure A indicates the results of examining the proportion of spleen-derived CD4-positive T cells following stimulation with $MOG_{35-55}$ in wild-type mice, MK-deficient mice, and MK-deficient mice treated with MK. Figure B indicates the results of analyzing FOXP3 mRNA expression in spleen-derived CD4-positive T cells from each of the above-mentioned groups by the real-time RT-PCR method following stimulation with $MOG_{35-55}$. The figures indicate relative values to FOXP3 mRNA expression in standard CD4-positive T cells.

[FIG. 5] The figure indicates the effect of the addition of MK on the dynamics of CD4-positive, CD25-positive T cells in MK-deficient mice. Figure A indicates the proportion of CD4-positive, CD25-positive regulatory T cells from each of the above-mentioned groups following stimulation of spleen-derived CD4-positive T cells with MOG$_{35-55}$. The CD4-positive part was gated, and only the CD4-positive cells were analyzed. Figure B indicates the results of analyzing FOXP3 mRNA expression in spleen-derived CD4-positive T cells from each of the above-mentioned groups by the real-time RT-PCR method following stimulation with MOG$_{35-55}$. The figures indicate values for GAPDH mRNA expression relative to FOXP3 mRNA expression.

FIG. 6 The figure indicates the Th1/Th2 balance in MK-deficient mice. FIG. A indicates the quantities of IFN-gamma and FIG. B indicates the quantities of IL-4 that are present in the culture supernatant of CD4-positive T cells that had been purified from murine splenocytes and cultured in the presence of MOG$_{35-55}$ (20 μg/mL). The values are expressed as mean±SEM for five mice. The Y-axis unit is pg/mL. The p value is calculated in accordance with the student t-test.

[FIG. 7] The figure indicates the results of analyzing the effect of the addition of anti-MK antibodies to the dynamics of CD4-positive, CD25-positive T cells in EAE model mice. The proportion of CD4-positive, CD25-positive T cells was detected after stimulating CD4-positive T cells derived from the spleens of EAE-induced mice with 30 μg/mL of MOG$_{35-55}$ and APC for five days in the presence of anti-MK antibodies (IP-13) or control antibodies (IgG).

[FIG. 8] The figure indicates the observed results of changes in clinical symptoms in EAE model mice resulting from the administration of anti-MK antibodies. Wild-type EAE model mice (C57BL-6, ♀, eight weeks old) were administered anti-MK antibodies (IP14), on days 0, 3, 7, 10, 14, 17, 21 and 24 (a total of eight times) following administration of MOG$_{35-55}$. The mice were divided into four groups (five mice per group), and were administered anti-MK antibodies in the caudal vein at the following doses per mouse weight (kg): group 1 (black diamond): 75 mg/kg; group 2 (black square) 7.5 mg/kg; group 3 (black triangle) 0.75 mg/kg; and group 4 (X, control) 0 mg/kg. The y-axis represents the mean values of clinical scores (0: no symptoms; 1: loss of tail tone; 2: laying face up, unable to rise; 3: unstable gait; 4: slight hind limb paralysis; 5: severe hind limb paralysis; 6: death).

[FIG. 9] The figure indicates the observed results of changes in clinical symptoms in EAE model mice resulting from the administration of MK aptamers. Wild-type EAE model mice (C57BL-6, ♀, eight weeks old) were administered intraperitoneally with aptamers for a total of ten doses every other day following administration of MOG$_{35-55}$. The doses of the aptamers were as follows: group 1 (black square): 15 mg/kg; group 2 (black triangle): 2.5 mg/kg; group 3 (X): 0.25 mg/kg; and group 4 (diamond, control): 0 mg/kg. The y-axis represents the mean values of clinical scores (0: no symptoms; 1: loss of tail tone; 2: laying face up, unable to rise; 3: unstable gait; 4: slight hind limb paralysis; 5: severe hind limb paralysis; 6: death). **: $p<0.01$.

BEST MODE FOR CARRYING OUT THE INVENTION

The inventors discovered that MK has the effect of inhibiting the increase in number of regulatory T cells and function of regulatory T cells, and that inhibition of MK expression or activity can eliminate the inhibitory activities. The present invention is based on these findings.

The present invention pertains to a therapeutic or preventive agent for diseases associated with the functional disorder of regulatory T cells comprising an MK inhibitor.

In the present invention, "MK inhibitor" may be a substance that inhibits MK expression or a substance that inhibits MK activity. An MK inhibitor is a substance that preferably has the effect of inhibiting binding activity of MK or MK receptors. In the present invention, "MK receptor" includes a complex consisting of receptor-type protein tyrosine phosphatase zeta, LRP (low-density lipoprotein receptor-related protein), ALK (anaplastic leukemia kinase) and syndecan. Inhibitors of the present invention may also be an inhibitor of the expression and/or activity of individual proteins of the complex.

For example, MK inhibitors of the present invention may be anti-MK antibodies, anti-MK receptor antibodies, aptamers against MK, antisense RNA against MK, dsRNA against MK and ribozymes against MK. Other examples of MK inhibitor include altered MK, soluble altered MK receptors, and dominant negatives of MK or MK receptors such as partial peptides of MK or MK receptors, as well as low-molecular substances that exhibit MK-inhibitory activity like as aforementioned inhibitors, but are not limited thereto. Preferred MK inhibitors of the present invention may be anti-MK antibodies, aptamers against MK, antisense RNA against MK, dsRNA against MK and ribozymes against MK. More preferably, MK inhibitors may be anti-MK antibodies and aptamers against MK.

Anti-MK antibodies and anti-MK receptor antibodies used in the present invention can be obtained by known method as polyclonal or monoclonal antibodies. The origin of the antibodies used in the present invention is not limited and is preferably mammal, and is more preferably human. Monoclonal antibodies derived from mammals include those produced by hybridomas, and those produced by hosts that have been transformed an expression vector containing antibody genes through genetic engineering methods. The antibodies bind to MK or MK receptors, thereby inhibiting MK binding to MK receptors and blocking the transmission of the biological signals of MK into cells. Such anti-MK antibodies include antibodies described in published references (Sun X. Z, et al., *J. Neuropathol Exp Neurol.* 56(12): 1339-48 (1997); Muramatsu H., et al., *J. Biochem* 119: 1171-77 (2004)).

Antibody-producing hybridomas can be produced as described below, basically utilizing known techniques. The hybridomas can be produced by using MK or MK receptors as the sensitizing antigen, immunizing them in accordance with a standard immunization protocol, fusing the obtained immune cells with known parent cells by a standard cell fusion method, and screening the monoclonal antibody-producing cells by a standard screening method.

Specifically, anti-MK antibodies can be produced as follows. For example, human MK, which is used as the sensitizing antigen to obtain antibodies, can be obtained by utilizing the MK gene/amino acid sequence disclosed in published references (Tomomura, M., et al., *J. Biol. Chem.* 265: 10765-10770 (1990); Tsutsui, J., et al., *Biochem. Biophys. Res. Commun.* 176: 792-797 (1991); Iwasaki, W., et al., *EMBO J.* 16(23): 6936-46 (1997)). SEQ ID NO.: 1 shows the sequence of the cDNA of the human-derived MK used in the method of the present invention; SEQ ID NO.: 2 shows the amino acid sequence of the MK encoded by the DNA.

Any MK receptor protein can be used as long as it can be used for the sensitizing antigen in producing the anti-MK receptor antibodies used in the present invention. The term "MK receptors" in the present invention refers to receptor complexes or each component (proteins of the complex).

MK protein used for the sensitizing antigen may be obtained by following method that the gene sequence of MK or MK receptor inserted in a known expression vector transforms host cell, and then the MK protein is purified by known means from the host cell or its culture supernatant. Alternatively, chemically synthesized MK protein (Inui, T., et al., *J. Peptide Sci.* 2: 28-39 (1996)) or MK receptor protein can be used as the sensitizing antigen. Furthermore, fused proteins that comprise MK protein or MK receptor protein and other protein can also be used as the sensitizing antigen.

Mammals to be immunized with the sensitizing antigen is not limited but is preferably selected by compatibility with the parent cells used in cell fusion. In general, rodents such as mice, rats and hamsters are used.

The animals are immunized with the sensitizing antigen in accordance with well-known methods. For example, in a general method, the sensitizing antigen is injected intraperitoneally or subcutaneously. Specifically, it is preferable that a suspension of the sensitizing antigen diluted by a suitable volume of PBS (phosphate-buffered saline), physiological saline, etc., is mixed with a suitable volume of standard adjuvant (e.g., complete Freund's adjuvant) if desired, emulsified and then administered in several doses every 4 to 21 days to a mammal. Suitable carriers may also be used when immunizing with a sensitizing antigen.

After the mammals have been immunized as described above, the elevation of the level of the desired antibody in the serum is verified, and the immune cells are removed from the animals to be used in cell fusion. Preferable immune cells for use in cell fusion may be splenocytes.

Mammalian myeloma cells which are suitable for use as the parent cells to be fused with the aforementioned immune cells include various known cell lines, such as: P3X63Ag8.653 (Kearney, J. F., et al., *J. Immunol.* (1979) 123: 1548-1550); P3X63Ag8U.1 (*Current Topics in Microbiology and Immunology* (1978) 81: 1-7); NS-1 (Kohler, G. and Milstein, C., *Eur. J. Immunol.* (1976) δ: 511-519); MPC-11 (Margulies, D. H., et al., *Cell* (1976) δ: 405-415); SP2/0 (Shulman, M. et al., *Nature* (1978) 276: 269-270); FO (de St. Groth, S. F., et al., *J. Immunol. Methods* (1980) 35: 1-21); S194 (Trowbridge, I. S., *J. Exp. Med.* (1978) 148: 313-323); and 8210 (Galfre, G., et al., *Nature* (1979) 277: 131-133).

The aforementioned cell fusion of immune cells and myeloma cells can be basically achieved by known means, such as the method developed by Milstein, et al. (Kohler, G. and Milstein, C.: *Methods Enzymol.* (1981) 73: 3-46).

More specifically, the cell fusion may be conducted, for example, in a standard nutrient culture solution in the presence of a cell fusion accelerator. Examples of used cell fusion accelerator include polyethylene glycol (PEG) and Sendai virus (HVJ). Furthermore, an adjuvant such as dimethylsulfoxide can be used if desired to enhance fusion efficiency.

The ratio of immune cells to myeloma cells to be used is, for example, preferably one to ten immune cells to one myeloma cell. The culture solution to be used in said cell fusion can be, for example, those preferable to proliferation of the myeloma cell strains such as RPMI 1640, MEM, and standard medium used for this type of cell culture. In addition, serum replacement fluid such as fetal calf serum (FCS) can be concomitantly used.

Cell fusion is achieved through the following method. The fused cells (hybridomas) are formed by thoroughly mixing the predetermined quantities of immune cells and myeloma cells in the culture medium, adding PEG solution (e.g., PEG solution with an approximate mean molecular weight of 1000 to 6000) preheated to approximately 37° C. at a concentration of 30 to 60% (w/v), and mixing. Then, a suitable medium is sequentially added, the mixture is centrifuged, and the supernatant is removed. Repetition of this process allows the removal of cell fusion accelerators and the others, which are undesirable for hybridoma growth.

Said hybridomas are selected by culturing them in standard selective medium such as HAT medium (a medium containing hypoxanthine aminopterin and thymidine). The cells are cultured in HAT medium for sufficient time for the death of cells (non-fused cells) other than the hybridomas, normally over a period of several days to several weeks. Next, by a standard limiting dilution method, the hybridomas that produce the antibodies are screened and cloned.

In addition to the above-mentioned method of using hybridomas by immunizing nonhuman animals with antigens, desired human antibodies of binding activity to desired antigens or antigen-expressing cells can be obtained by sensitizing human lymphocytes in vitro with the desired antigen protein or antigen-expressing cells, and fusing the sensitized B lymphocytes with human myeloma cells, e.g., U266 (see Japanese published examined application No. H01-59878). Furthermore, the desired human antibodies may be obtained in accordance with the method by administering the antigens or antigen-expressing cells to transgenic animals having a human antibody gene repertoire (see international publication numbers WO93/12227, WO92/03918, WO94/02602, WO94/25585, WO96/34096 and WO96/33735).

Hybridomas that produce monoclonal antibodies, which are produced said manner, can be sub-cultured in standard medium, and can be stored for extended periods in liquid nitrogen.

Methods to obtain monoclonal antibodies from said hybridomas include the following methods: culturing said hybridomas in accordance with standard methods and obtaining the antibodies from the culture supernatant; or proliferating the hybridomas by administering them to compatible mammals and obtaining the antibodies from the peritoneal fluid. The former method is suitable for obtaining highly pure antibodies; meanwhile, the latter method is suitable for mass production of antibodies.

The monoclonal antibodies of the present invention may be recombinant antibodies produced using recombinant gene technology by cloning antibody genes from hybridomas, inserting them into suitable vectors, and transforming them into a host (e.g., see Borrebaeck, C. A. K., and Larrick, J. W., *Therapeutic Monoclonal Antibodies*, published in the United Kingdom by Macmillan Publishers Ltd., 1990).

Specifically, the mRNA that encodes the variable (V) region of the antibody is isolated from the cells that produce the antibodies, e.g., hybridomas. To isolate the mRNA, total RNA is prepared by a known method such as the guanidine ultracentrifugation method (Chirgwin, J. M., et al., *Biochemistry* (1979) 18: 5294-5299) and the AGPC method (Chomczynski, P., et al., *Anal. Biochem.* (1987) 162: 156-159); the mRNA is prepared using the mRNA Purification Kit (manufactured by Pharmacia Corporation), or other kits. The mRNA may also be prepared directly using the QuickPrep mRNA Purification Kit (manufactured by Pharmacia Corporation).

The cDNA of the antibody V region is synthesized from the obtained mRNA using reverse transcriptase. The cDNA can be synthesized using the AMV Reverse Transcriptase First-strand cDNA Synthesis Kit, or other kits. Also, cDNA can be synthesized and amplified using the 5'-Ampli Finder RACE Kit (manufactured by Clontech) and the 5'-RACE method that utilizes PCR (Frohman, M. A., et al., *Proc. Natl. Acad. Sci. USA* (1988) 85: 8998-9002; Belyaysky, A., et al., *Nucleic Acids Res.* (1989) 17: 2919-2932). The target DNA fragment is purified from the obtained PCR product, and is coupled to vector DNA. These are used to prepare recombinant vectors, which are then introduced into *E. coli* or others, and a colony is selected to prepare the desired recombinant vector. The base sequence of the target DNA is verified using well known methods, such as the deoxy method.

When the DNA that encodes the V region of the target antibodies is obtained, it is coupled to DNA that encodes the constant (C) region of the desired antibodies, and then inserted into the expression vector. Alternatively, the DNA that encodes the V region of the antibodies may be inserted into an expression vector that contains the DNA of the C region of the antibodies.

In order to produce the antibodies used in the present invention, the antibody genes may be inserted into expression vectors so that they are expressed in the expression control region, e.g., under enhancer and/or promoter control. Then, the host cells are transformed by this expression vector to express the antibodies.

In the present invention, artificial gene recombinant antibodies, such as chimeric antibodies, humanized antibodies and human antibodies can be used in order to reduce heteroantigenicity to humans. These altered antibodies can be prepared using well known method.

Chimeric antibodies can be produced by coupling DNA that encodes the V region of antibodies obtained as described above to DNA that encodes the C region of human antibodies, inserting them into expression vectors and introducing them into hosts (see European patent application laid-open number EP125023 and international publication number WO92/19759). Chimeric antibodies useful in the present invention can be obtained utilizing this well known method.

Humanized antibodies are also called reshaped human antibodies or human type antibodies; they are obtained by transplanting the complementarity determining region (CDR) of antibodies of nonhuman mammals, such as mice, into the human antibody CDR, and the general gene recombination method thereof is known (see European patent application laid-open number EP125023 and international publication number WO92/19759).

Specifically, a DNA sequence designed to connect the murine antibody CDR to the human antibody framework region (FR) is synthesized by means of the PCR method from several oligonucleotides that have been prepared so that they have overlapping parts at their ends. The obtained DNA is coupled to DNA that encodes the human antibody C region, and is then inserted into an expression vector, followed by transformation to a host to produce the antibodies (see European patent application laid-open number EP239400 and international publication number WO92/19759).

The human antibody FR coupled via the CDR is selected as complementarity determining region (CDR) forms a good antigen-binding site. The amino acids in the framework region of the antibody variable region may be substituted as needed so that the complementarity determining region of the reshaped human antibodies forms a suitable antigen-binding site (Sato, K. et al., *Cancer Res*. (1993) 53: 851-856).

The human antibody C region is used for chimeric antibodies and humanized antibodies. One example of the human antibody C region is C-gamma; for example, C-gamma 1, C-gamma 2, C-gamma 3 or C-gamma 4 can be used. Furthermore, the human antibody C region may be modified to improve the stability or productivity of the antibody.

Chimeric antibodies consist of the V region of nonhuman mammal-derived antibodies and the C region of human antibody. Humanized antibodies consist of the complementarity determining region of nonhuman mammal-derived antibodies and the framework region and C region of human antibody. Antigenicity of these antibodies in the human body are reduced and then these antibodies are useful as antibodies to be used in the present invention.

There are several methods for obtaining human antibodies. In addition to the method set forth above, the technique of obtaining human antibodies by panning the human antibody library is known. For example, phages expressing the variable region of a human antibody on a surface as a single chain antibody (scFv) by phage display method are applied to select of phages which bind to antigens. The DNA sequence that encodes the variable region of the human antibodies that bind to the antigen can be determined by analyzing the genes of the selected phage. Once the DNA sequence of the scFv that binds to the antigen is determined, a suitable expression vector with said sequence can be produced to obtain the human antibodies. These methods are well known, and can be referenced in WO92/01047, WO92/20791, WO93/06213, WO93/11236, WO93/19172, WO95/01438 and WO95/15388.

Antibody genes constructed as described above can be expressed to obtain the antibodies by well known methods. In the case of using mammalian cells, the antibodies can be expressed by the DNA functionally constructed of a commonly employed useful promoter, the antibody gene to be expressed, and a poly-A signal attached downstream on its 3' end, or by vectors that contain said DNA. An example of a promoter/enhancer may be the human cytomegalovirus immediate early promoter/enhancer.

Other promoter/enhancers that can be used expression of antibody expression that are used in the present invention include viral promoter/enhancers such as retroviruses, polyomaviruses, adenoviruses and simian virus 40 (SV40); and mammalian cell-derived promoter/enhancers such as human elongation factor 1 alpha (HEF1alpha).

For example, antibodies can be expressed easily by means of the method developed by Mulligan, et al. (Mulligan, R. C. et al., *Nature* (1979) 277: 108-114), using the SV40 promoter/enhancer, and by means of the method developed by Mizushima, et al. (Mizushima, S, and Nagata, S., *Nucleic Acids Res*. (1990) 18: 5322), using the HEF1alpha promoter/enhancer.

In the case of using *E. coli*, antibodies can be expressed by the DNA functionally constructed of a commonly employed useful promoter, a signal sequence for antibody secretion, and the gene of the antibody to be expressed. Examples of promoters include the lacZ promoter and araB promoter. Antibodies can be expressed by means of the method developed by Ward, et al. (Ward, E. S. et al., *Nature* (1989) 341: 544-546; Ward, E. S. et al., *FASEB J*. (1992) 8: 2422-2427), employing the lacZ promoter; and by means of the method developed by Better, et al. (Better, M. et al., *Science* (1988) 240: 1041-1043), employing the araB promoter.

When producing antibodies in *E. coli* periplasm, the pelB signal sequence (Lei, S. P. et al., *J. Bacteria* (1987) 169: 4379-4383) can be used as the signal sequence for antibody secretion. The antibodies can be used by refolding the antibody structure properly after isolating the antibodies produced in the periplasm (e.g., see WO96/30394).

Replication origins derived from SV40, polyomaviruses, adenoviruses, and bovine papillomaviruses can be used as the replication origin. Furthermore, for gene replication and amplification in a host cell line, the expression vector can contain the aminoglycoside phosphotransferase (APH) gene, thymidine kinase (TK) gene, *E. coli* xanthine-guanine phosphoribosyl transferase (Ecogpt) gene, dihydrofolate reductase (dhfr) gene, and others as the selection marker.

Any generating system can be used in the production of antibodies to be used in the present invention. Generating systems for antibody production may be in vitro or in vivo system. Examples of an in vitro generating system include a generating system that utilizes eukaryotic cells and one that utilizes prokaryotic cells.

The generating systems that employ eukaryotic cells may employ animal cells, plant cells, or fungal cells. Animal cells known well to be employed in the generating systems include: (1) mammalian cells, e.g., CHO, COS, myeloma, BHK (baby hamster kidney), HeLa and Vero; (2) amphibian cells, e.g., *Xenopus* oocytes; and (3) insect cells, e.g., sf9, sf21 and Tn5. Plant cells known well to be employed in the generating systems include *Nicotiana tabacum*-derived cells, which can be cultured in a callus culture. Fungal cells known well to be employed in the generating systems include yeasts, e.g., those belonging to the genus *Saccharomyces*, such as *Saccharomyces cerevisiae*; filamentous fungi, e.g., those belonging to the genus *Aspergillus*, such as *Aspergillus niger*.

The generating systems that employ prokaryotic cells may employ bacterial cells. Bacterial cells known well to be employed in the generating systems include *E. coli* and *Bacillus subtilis*.

Antibodies are obtained by introducing the target antibody gene into these cells by means of transformation, and culturing the transformed cells in vitro. The cells are cultured in accordance with known methods. For example, DMEM, MEM, RPMI 1640 and IMDM can be used as the culture medium, and a serum replacement fluid such as fetal calf serum (FCS) can be used concomitantly. Antibodies may also be produced in vivo by transferring the cells introduced antibody genes into the peritoneum or other part of an animal. Examples of in vivo generating systems include those that employ animals or plants. Generating systems that employ animals may employ mammals or insects.

Mammals such as goats, pigs, sheep, mice and cows, and insects such as silkworms can be used in vivo generating systems (in Vicki Glaser, SPECTRUM Biotechnology Applications, 1993). And plants such as Indian weed (*Nicotiana tabacum*) can be used.

After introduction of the antibody genes into these animals or plants, the antibodies are produced in the bodies of the animals or plants, and then collected. For example, the antibody gene is introduced into the gene that encodes a protein uniquely produced in milk, such as goat beta casein, and prepared as a fused gene. DNA fragments containing the fused gene containing the antibody gene are injected into a goat embryo, and this embryo is introduced into a female goat. The desired antibodies are obtained from the milk produced by the transgenic goat, which is born from the goat implanted with the embryo, or its offspring. If necessary, hormones may be used on the transgenic goat in order to increase the volume of milk containing the desired antibodies that is produced by the transgenic goat (Ebert, K. M. et al., *Bio/Technology* (1994) 12: 699-702).

When using silkworms, the silkworms can be infected with baculoviruses inserted the target antibody gene, and the desired antibodies are obtained from the silkworm humor (Maeda, S. et al., *Nature* (1985) 315: 592-594). When using Indian weed, the target antibody gene is inserted into a plant expression vector, such as pMON530, and this vector is introduced into bacteria such as *Agrobacterium tumefaciens*. The Indian weed, e.g., *Nicotiana tabacum*, is infected with these bacteria, and the desired antibodies are obtained from the leaves of the Indian weed (Julian, K.-C. Ma et al., *Eur. J. Immunol.* (1994) 24: 131-138).

When producing antibodies by in vitro or in vivo generating system as above, the DNA that encodes the heavy chain (H chain) and the DNA that encodes the light chain (L chain) of the antibodies can be separately inserted into discrete expression vectors and both of the vectors may be simultaneously transformed into the host cells. The DNA that encodes the H chain and the L chain can be inserted into a single expression vector and the vector may be transformed into the host cells (see international publication number WO94/11523).

The produced antibodies as above can be isolated from the host intracellularly or extracellularly, and be purified until they are homogeneous. The isolation and purification of the antibodies to be used in the present invention can be achieved through affinity chromatography. Columns to be used for affinity chromatography include, for example, the protein A column and protein G column. Carriers employed in the protein A column include, for example, HyperD, POROS and Sepharose FF. Other standard protein isolation and purification methods may also be employed and not limited to the above.

For example, the antibodies used in the present invention can be isolated and purified by selecting and/or combining methods such as types of chromatography other than the above-mentioned affinity chromatography, filtration, ultrafiltration, salting out and dialysis. Types of chromatography include, for example, ion-exchange chromatography, hydrophobic chromatography and gel filtration. These types of chromatography can be applied to HPLC (high-performance liquid chromatography). Reverse phase HPLC may be employed as well.

The concentration of the antibodies obtained as described above can be assayed by methods such as absorbance assay or ELISA. When employing absorbance assay, the antibody solution appropriately diluted with PBS (−) is measured its absorbance at 280 nm, and then the concentration is calculated as 1.35 OD=1 mg/mL. When employing ELISA, 100 μL of goat anti-human IgG (produced by TAG) that has been diluted to 1 mg/mL with 0.1 M bicarbonate buffer solution (pH=9.6) is applied to a 96-well plate (manufactured by Nunc), and then incubated overnight at 4° C. to immobilize the antibodies.

After blocking step, a 100 micro-L aliquot, samples containing the antibody or properly diluted antibody that is used in the present invention, or containing human IgG (produced by Cappel) as a standard, is added to each well, and then incubated for one hour at room temperature.

After washing, 100 μL of a 1:5000 dilution of alkaline phosphatase-labeled anti-human IgG (produced by BioSource) is added to each well, and then incubated for one hour at room temperature. After washing, a substrate solution is added, and then the samples are incubated again. The absorbance is then measured at 405 nm using the Microplate Reader Model 3550 (manufactured by Bio-Rad), and the concentration of the target antibodies is calculated.

In the present invention, the term "aptamer" refers to nucleic acids that bind to various molecules such as proteins and hormones. The term, MK aptamer refers to nucleic acids that bind to MK. The term, MK aptamer inhibitor refers to nucleic acids that bind to MK, thereby inhibiting the MK from binding to molecules that bind to MK, such as MK receptors and extracellular matrices. MK aptamers may be RNA or DNA; there are no particular limitations to the RNA and DNA as long as it binds to MK. Nucleic acids, whose ribose, phosphate backbone, nucleic acid base, or/and 5' or/and 3' end has been modified, may be included in said RNA and DNA, and; there is no limitation as long as these nucleic acids bind to MK. The nucleic acid chain may be single- or double-stranded, but single-stranded chain is preferable.

There is no limitation to the length of the aptamer, as long as it is long enough to bind specifically to the target molecule;

however, they may consist of 10 to 200 nucleotides, preferably 10 to 100 nucleotides, more preferably 15 to 80 nucleotides, and the most preferably 15 to 50 nucleotides.

Aptamers comprising nucleotides alone can be used as a therapeutic agent, and also those bound to other molecules, such as polyethylene glycol, cholesterol, peptides, liposome, fluorescent pigment, radioactive substance, toxin or another aptamer, can be used. In the present invention, the term "aptamer" includes such aptamers to which other molecules are bound.

Aptamers in the present invention can be selected utilizing methods known well by a person skilled in the art. It is not intended to limit the method, but aptamers can be selected by, for example, the SELEX method (systematic evolution of ligands by exponential enrichment) (Tuerk, C. and Gold, L., 1990, Science, 249: 505-510). The SELEX method is a method wherein a nucleic acid pool having approximately $10^{15}$ different nucleotide sequences, is mixed with a target substance, and then nucleic acids that bind to or strongly bind to the target substance are selected. The selected nucleic acids are amplified by RT-PCR or PCR, and are used as the template for the next round. Approximately ten repetitions of these steps yield the target aptamers. When using aptamers as a drug, minimizations in size and stabilization are required. Practically, they can be minimizing in size by eliminating nucleotides that have no effect on their activity, and can be stabilized by modification. The half life of natural RNA in serum is several seconds, however, the half life can be extended to one week or longer by, for example, O-methylation on the 2'-position of ribose and binding inverted dT to the both ends of the RNA.

The "antisense RNA against MK" in the present invention is a complementary antisense RNA to the transcription product of DNA encoding MK, for example, the antisense RNA described in Japanese published unexamined patent applications 2002-142778 and 2003-012447. There are multiple factors for the action by which antisense nucleic acids suppress the expression of target genes. These factors include inhibition of transcription initiation by triple strand formation, inhibition of transcription by hybrid formation at the site where the RNA polymerase has formed a local open loop structure, transcription inhibition by hybridization with the RNA being synthesized, inhibition of splicing by hybrid formation at the junction between an intron and an exon, inhibition of splicing by hybrid formation at the site of spliceosome formation, inhibition of mRNA translocation from the nucleus to the cytoplasm by hybridization with mRNA, inhibition of splicing by hybrid formation at the capping site or at the poly (A)-addition site, inhibition of translation initiation by hybrid formation at the binding sites for translation initiation factors, translation inhibition by hybrid formation with the ribosome binding site near the initiation codon, inhibition of peptide chain elongation by hybrid formation in the translated region or at the polysome-binding sites of mRNA, and inhibition of gene expression by hybrid formation at the sites of interaction between nucleic acids and proteins. These factors inhibit target gene expression by inhibiting the processes of transcription, splicing, or translation.

The antisense sequences used in the present invention may inhibit target gene expression by any of the actions set forth above. In one embodiment an antisense sequence designed to be complementary the untranslated region near from the 5' site of the MK gene mRNA would effectively inhibit gene translation. Also, sequences that are complementary to the code region or the 3' untranslated region can be used as well. DNA containing not only the translated region of the gene but also the antisense sequence of the untranslated region is included in the antisense DNA used in the present invention. The antisense DNA to be used is coupled to a downstream site from a suitable promoter, and preferably, a sequence containing a transcription termination signal is coupled at 3' site. DNA prepared in this manner can transform desired plants by well known methods. It is preferable that the antisense DNA sequence is complementary to the endogenous gene of the plant to be transformed or to a part thereof, but does not need to be completely complementary as long as it can effectively inhibit gene expression. The transcribed RNAs may be preferably at least 90%, or more preferably at least 95% complement to the transcription product of the target gene. In order to effectively inhibit target gene expression using antisense sequence, the length of the antisense DNA may be at least 15 bases, preferably at least 100 bases, and more preferably at least 500 bases. Usually, the length of the antisense DNA to be used is shorter than 5 kb, preferably shorter than 2.5 kb.

The "dsRNA against MK" used in the present invention refers to a double-stranded RNA that inhibits MK gene expression by RNA interference (RNAi), for example, the dsRNA described in Japanese published unexamined patent application 2004-275169. RNA interference is a phenomenon by which introduction of a dsRNA having the same or similar sequence to the target gene sequence into a cell inhibits expression of both of the introduced exogenous gene and the target endogenous gene. When dsRNA of approximately 40 to several hundred base pairs is introduced into a cell, an RNase III-type nuclease called a Dicer having a helicase domain cleaves the dsRNA from the 3' end in units of approximately 21 to 23 bases, producing siRNA (short interference RNA). Specific proteins bind to said siRNA, forming a nuclease complex (RISC: RNA-induced silencing complex). This complex recognizes and binds to sequences that are the same as those of siRNA, and cleaves the mRNA of the target gene at the center of siRNA by RNase III-type enzyme activity. Separately from this mechanism, the antisense strand of the siRNA is thought to bind to the mRNA and acts as the RNA-dependent RNA polymerase (RsRP) primer, synthesizing dsRNA, and this dsRNA, in turn, becomes the substrate for the Dicer, producing new siRNA, thus amplifying the effect.

Examples of the dsRNA in the present invention include siRNA and shRNA. The term "siRNA" refers to a double-stranded RNA consisting of short strands within the scope not to indicate intracellular toxicity, for example, 15 to 49 base pairs, preferably 15 to 35 base pairs, and more preferably 21 to 30 base pairs. Alternatively, the expressed siRNA is transcribed, and the final length of the double-stranded RNA can be, for example, 15 to 49 base pairs, preferably 15 to 35 base pairs, and more preferably 21 to 30 base pairs. The term "shRNA" refers to siRNA wherein a single-stranded RNA consists of a double strand by forming hairpin structure.

It is not necessary for the dsRNA to be completely identical to the target gene, but their sequences may be no less than 70%, preferably no less than 80%, more preferably no less than 90%, and most preferably no less than 95% homologous.

The double-stranded RNA in the dsRNA includes but not limited to those with perfect pairing, and may contain unpaired portions resulting from mismatches (wherein the paired bases are not complementary) or bulges (wherein bases that pair with bases of one strand are missing from the other strand). In the present invention, the double-stranded RNA region in the dsRNA where the RNAs are paired may contain both bulges and mismatches.

The term "ribozymes against MK" refers to nucleic acids having catalytic activity that affect MK expression and function, and includes nucleic acids that specifically cleave MK mRNA.

In addition, some of MK activity requires dimerization of MK through the amino end domain (Kojima, S., et al., *J. Biol. Chem.*, 272: 9410-9416 (1997)), therefore a partial peptide of MK (e.g., a part of the amino end domain of MK) can also be used as an MK inhibitor.

Also, there is a retinoic acid receptor-binding site in the 5' upstream region of the human and murine MK gene, and MK is a product of a gene responsive to retinoic acid (Matsubara, S., et al., *J. Biochem.* 115: 1088-1096 (1994)). Thus, retinoic acid inhibitors can also be used as an MK inhibitor.

Furthermore, WT1 known as a Wilms' tumor suppressor gene, inhibits expression of downstream genes of MK promoters (Adachi, Y., et al., *Oncogene* 13: 2197-2203 (1996)) and can also be used as an MK inhibitor.

In addition, MK binds strongly to molecules such as MK receptors, chondroitin sulfate and heparin (Ueoka, C., et al., *J. Biol. Chem.* 275: 37407-37413 (2000)), and these molecules as well as portions of these molecules can also be used as an MK inhibitor.

Furthermore, an MK inhibitor that inhibits MK expression and/or activity can be obtained by means of the screening method described herein below.

The term "treatment or prevention of diseases associated with the functional disorder of regulatory T cells" in the present invention refers to the inhibition or prevention of symptoms of diseases associated with the functional disorder of regulatory T cells, and/or symptoms of complicating diseases associated with the functional disorder of regulatory T cells.

The term "diseases associated with the functional disorder of regulatory T cells" in the present invention refers to diseases associated with the reduction in the number of regulatory T cells in the body, or diseases associated with the reduced functioning of regulatory T cells. "Diseases associated with the functional disorder of regulatory T cells" in the present invention are preferably diseases that are associated with the functional abnormality of CD4-positive, CD25-positive regulatory T cells.

Examples of diseases associated with the functional abnormality of regulatory T cells include multiple sclerosis, autoimmune diseases, allergic diseases, chronic transplant rejection, inflammatory colitis, type 1 diabetes, amyotrophic lateral sclerosis, chronic rheumatoid arthritis, systemic lupus erythematosus (SLE), myasthenia gravis, progressive systemic sclerosis (PSS), Sjögren's Syndrome, polymyositis (PM), dermatomyositis (DM), polyarteritis nodosa (PN), thyroid abnormality, Graves' disease, Guillian-Barre Syndrome, primary biliary cirrhosis (PBC), idiopathic thrombocytopenic purpura, autoimmune hemolytic anemia in inflammatory colitis, and Crohn's disease, and are preferably autoimmune diseases, allergic diseases, chronic transplant rejection, inflammatory colitis, type 1 diabetes, multiple sclerosis, amyotrophic lateral sclerosis and myasthenia gravis. Multiple sclerosis can be one of the preferable diseases which are treated in the present invention.

The "an expansive agent for regulatory T cell population" or "therapeutic or preventive agent for diseases associated with the functional disorder of regulatory T cells" of the present invention is effective particularly against the above-mentioned diseases which are diagnosed as being caused by the reduction of the number of regulatory T cells.

The an expansive agent for regulatory T cell population and therapeutic or preventive agent for diseases associated with the functional disorder of regulatory T cells of the present invention may include pharmacologically acceptable excipients such as preservatives and stabilizers. Such pharmacologically acceptable excipients can be excipients that are pharmacologically permissible and can be administered with the above-mentioned an expansive agent for regulatory T cell population and/or therapeutic agent, wherein the excipients themselves have the above-mentioned increasing effect for regulatory T cells or therapeutic effect against diseases associated with the functional abnormality of regulatory T cells, or wherein the excipients which do not have said increasing effect or therapeutic effect. The excipients may not have the above-mentioned increasing effect for regulatory T cells or therapeutic effect against diseases associated with the functional abnormality of regulatory T cells, but may have a synergistic or additive stabilizing effect when used concomitantly with an MK inhibitor.

For example, pharmacologically acceptable ingredients include sterilized water, physiological saline solution, stabilizers, fillers, buffering agents, preservatives, surfactants, chelating agents (e.g., EDTA) and binders.

Surfactants used in the present invention include nonionic surfactants, for example, sorbitan fatty acid esters, such as sorbitan monocaprylate, sorbitan monolaurate and sorbitan monopalmitate; and glycerin fatty acid esters with an HLB value of 6 to 18, such as glycerin monocaprylate, glycerin monomyristate and glycerin monostearate.

The surfactants may also be anionic surfactants. These include alkylsulfates having an alkyl group of 10 to 18 carbon atoms, such as sodium cetylsulfate, sodium laurylsulfate and sodium oleylsulfate; polyoxyethylene alkylethersulfate salts having an alkyl group of 10 to 18 carbon atoms whose mean number of moles of added ethyleneoxides is 2 to 4, such as sodium polyoxyethylene laurylsulfate; an alkylsulfosuccinate ester salt whose alkyl group has 8 to 18 carbon atoms, such as sodium laurylsulfosuccinate ester; natural surfactants, such as lecithin and glycerophospholipid; sphingophospholipids such as sphingomyelin; and sucrose fatty acid esters whose fatty acids have 12 to 18 carbon atoms.

One or a combination of two types of these surfactants may be added to the composition of the present invention. Preferable surfactants used in the formulation of the composition of the present invention are polyoxyethylene sorbitan fatty acid esters, such as polysorbate 20, 40, 60 or 80; preferably polysorbate 20 and 80. Polyoxyethylene polyoxypropylene glycols, such as poloxamer (such as Pluronic F68 (Registered Trademark)) are also preferable.

Buffering agents of the present invention include phosphoric acid, citric acid buffer solution, acetic acid, malic acid, tartaric acid, succinic acid, lactic acid, potassium phosphate, gluconic acid, caprylic acid, deoxycholic acid, salicylic acid, triethanolamine, fumaric acid, and other organic acids; and carbonate buffer solution, tris buffer solution, histidine buffer solution, and imidazole buffer solution.

Solution formulations may be prepared by dissolving the drug in an aqueous buffer solution known well in the field of solution formulation. The concentration of the buffer solution is generally 1 to 500 mM, preferably 5 to 100 mM, and more preferably 10 to 20 mM.

The drug in the present invention may also contain other ingredients such as polypeptides of low molecular weight, serum albumin, proteins such as gelatin and immunoglobulin, amino acids, sugars and carbohydrates such as polysaccharides and monosaccharides, and sugar alcohols.

For example, sugars and carbohydrates such as polysaccharides and monosaccharides of the present invention include dextran, glucose, fructose, lactose, xylose, mannose, maltose, sucrose, trehalose and raffinose.

For example, sugar alcohols of the present invention include mannitol, sorbitol and inositol.

The pharmaceutical composition in the formulation of an injectable aqueous solution may include solvents such as physiological saline solution, isotonic solutions containing glucose or other adjuvants, such as D-sorbitol, D-mannose, D-mannitol and sodium chloride. Suitable solubilizing agents such as alcohol (e.g., ethanol), polyalcohol (e.g., propylene glycol and PEG) and nonionic surfactants (e.g., polysorbate 80, HCO-50) may be used concomitantly.

The drug may also contain diluents, solubilizing agents, pH adjusters, soothing agents, sulfur-containing reducing agents, antioxidants, etc. if desired.

Furthermore, the drug may be contained in microcapsules (microcapsules formed of hydroxymethylcellulose, gelatin, poly[methylmethacrylic]acid, etc.), or may be delivered in the form of a colloidal drug delivery system (liposome, albumin microsphere, microemulsion, nanoparticles, nanocapsules, etc.) if needed (see *Remington's Pharmaceutical Science* 16$^{th}$ *Edition*, Oslo Ed., 1980, etc.). Methods for forming sustained-release formulation are also well known, and may be applied to the present invention (Langer et al., *J. Biomed. Mater. Res.* 1981, 15: 167-277; Langer, Chem. Tech. 1982, 12: 98-105; U.S. Pat. No. 3,773,919; European patent application laid-open numbers EP58481 and EP133988; Sidman et al., *Biopolymers* 1983, 22: 547-556). Pharmacologically permissible carriers to be used may be selected from the above-mentioned list depending on the form of the drug, either singly or in combination, but are not limited thereto.

The present invention pertains to a method for screening a pharmaceutical composition for the treatment or prevention of disease associated with the functional disorder of regulatory T cells by inhibiting MK expression or activity.

In the present invention, the description "inhibit MK expression" includes inhibition of gene transcription as well as inhibition of translation into proteins. Furthermore, it encompasses not only the complete termination of DNA expression but also a reduction in such expression.

In the first embodiment of the screening method of the present invention, a plurality of test compounds is contacted with MK.

SEQ ID NO.: 1 shows the sequence for the cDNA of the human-derived MK used in the method of the present invention; SEQ ID NO.: 2 shows the amino acid sequence for the MK encoded by said DNA. The MK used in the method of the present invention includes functionally equivalent proteins to the above-mentioned well known MK. For example, such proteins include MK mutants, alleles, variants, homologs, partial MK peptides and proteins fused with other proteins, but are not limited thereto.

MK mutants of the present invention may be naturally derived proteins comprising amino acid sequences wherein one or a plurality of amino acids in the amino acid sequence set forth in SEQ ID NO.: 2 has been substituted, deleted, inserted and/or added, that are functionally equivalent to the protein comprising the amino acid sequence set forth in SEQ ID NO.: 2. Proteins encoded by naturally derived DNA which hybridize with DNA of the sequence set forth in SEQ ID NO.: 1 under stringent conditions that are functionally equivalent to the protein comprising the amino acid sequence set forth in SEQ ID NO.:2 are also included in the MK mutants.

In the present invention, there is no particular limitation for the number of mutated amino acids; however, it may be within 30 amino acids, preferably within 15 amino acids, and more preferably within 5 amino acids (for example, within 3 amino acids).

It is desirable that the side chains of the mutated amino acid residues preserve the properties of the original amino acid side chains. Properties of amino acid side chains may be, for example: hydrophobic amino acids (A, I, L, M, F, P, W, Y, V); hydrophilic amino acids (R, D, N, C, E, Q, G, H, K, S, T); amino acids having an aliphatic side chain (G, A, V, L, I, P); amino acids having a side chain containing a hydroxy group (S, T, Y); amino acids having a side chain containing a sulfur atom (C, M); amino acids having a side chain containing carboxylic acid and an amide (D, N, E, Q); amino acids having a side chain containing a base (R, K, H); and amino acids having a side chain containing an aromatic group (H, F, Y, W) (the letters in parentheses are single-letter representations of amino acids). It is well known that a polypeptide of an amino acid sequence wherein a single amino acid or a plurality of amino acids of a given amino acid sequence has been modified by deletion, addition and/or substitution by another amino acid maintains the biological activity of the given amino acid sequence.

In the present invention, the term "functionally equivalent" refers the biological and biochemical functional equivalence of the protein to MK. In the present invention, the biological and biochemical functions of MK include promotion of cell proliferation (promotion of fibroblast, keratinocyte or tumor cell proliferation), enhancement of cell survival (enhancement of survival of fetal neurons or tumor cells), promotion of cell migration (promotion of neuron, neutrophil, macrophage, osteoblast or vascular smooth myocyte migration), promotion of chemokine expression, promotion of angiogenesis and promotion of synapse formation. Biological properties include specificity of expression-site and expression level.

Methods for preparing DNA that encodes a "protein that is functionally equivalent" to the target protein known well to those skilled in the art include methods that utilize hybridization or polymerase chain reaction (PCR) techniques. For example, those skilled in the art can isolate DNA highly homologous to MK using the MK base sequence (SEQ ID NO.: 1) or a part thereof as the probe, or using an oligonucleotide that specifically hybridizes with MK (SEQ ID NO.: 1) as the primer. The DNA isolated by above-mentioned hybridization or PCR techniques that encodes a protein that is functionally equivalent to MK, is also included in the DNA of the present invention.

Such DNA is isolated by means of a hybridization reaction, preferably under stringent conditions. In the present invention, the expression "stringent hybridization conditions" refers to hybridization conditions of 6 M urea, 0.4% SDS and 0.5×SSC, or hybridization conditions with an equivalent stringency thereto. Even more highly homologous DNA can be expected to be isolated by employing even more highly stringent conditions, e.g., 6 M urea, 0.4% SDS and 0.1×SSC. Isolated DNA in such a manner is believed to be highly homologous at the amino acid level to the amino acid sequence of the target protein. The expression "highly homologous" refers to sequence homologousness of at least 50% or higher, preferably 70% or higher, more preferably 90% or higher (e.g., 95%, 96%, 97%, 98%, 99% or higher) to the overall amino acid sequence. The identities of amino acid sequences and base sequences can be determined by utilizing the BLAST algorithm developed by Carlin and Altschul (*Proc. Natl. Acad. Sci. USA* 87: 2264-2268, 1990; *Proc. Natl. Acad. Sci. USA* 90: 5873, 1993). Programs such as BLASTN and BLASTX based on BLAST algorithm have been developed (Altschul, S. F. et al.: *J. Mol. Biol.* 215: 403, 1990).

When analyzing base sequences using BLASTN, the parameters may be, for example, score=100 and wordlength=12. When analyzing amino acid sequences using BLASTX, the parameters may be, for example, score=50 and wordlength=3. When using the BLAST and the gapped BLAST programs, the parameters may be the default parameters for the respective programs. Specific techniques of these analytical methods are well known.

There is no limitation to the species from which the MK used in the present invention derived. The MK can be derived from, but not limited to, humans, monkeys, mice, rats, guinea pigs, pigs, cows, yeast and insects.

The state of the MK employed in the first embodiment is not limited and, for example, can be purified form, expressed form in cells, expressed form in cell extracts.

MK can be purified by well known methods. Cells to express MK include cells expressing endogenous MK and cells expressing exogenous MK. The above-mentioned cells expressing MK include cultured cells, but are not limited thereto. There is no particular limitation to the above-mentioned cultured cells and, for example, commercially available cells can be used. The species from which the cells expressing endogenous MK are derived are not limited to, but include humans, monkeys, mice, rats, guinea pigs, pigs, cows, yeast or insects. The above-mentioned cells expressing exogenous MK can be produced, for example, by introducing a vector containing the DNA that encodes MK into a cell. The vector can be introduced into a cell by standard methods, such as the calcium phosphate precipitation method, electroporation method, Lipofectamine method and microinjection method. The above-mentioned cells having exogenous MK can be produced, for example, by inserting DNA that encodes MK into a chromosome using a gene introduction method that utilizes homologous recombination. Species of cells into which exogenous MK is inserted are not limited to mammals, but include a technique for expressing exogenous proteins the cells in which has been established.

For example, the cell extracts in which MK is expressed may be a cell extract of an in vitro transcription-translation system added a vector including DNA encoding MK. Said in vitro transcription-translation system is not limited but can be commercially available in vitro transcription-translation kits.

The "test compound" in the method of the present invention is not limited but may be, for example: single compounds such as natural compounds, organic compounds, inorganic compounds, nucleic acids, proteins and peptides; as well as a compound library, nucleic acid library, peptide library or gene expression products library, cell extracts, cell culture supernatant, fermentation microbe products, marine organism extracts, plant extracts, prokaryotic cell extracts, eukaryotic unicellular organism extracts, and animal cell extracts. The above test samples can be labeled if needed. Examples of labels include radiolabels and fluorescent labels. In addition to the above-mentioned test samples, mixtures of a plurality of these test samples can be used.

In the present invention "contacting" may be achieved depending on the state of MK. For example, if the MK is purified, the test sample can be contacted with the MK by adding the test sample to the purified preparation. If the MK is expressed in cells or in cell extracts, the test sample can be contacted with the MK by adding the test sample to the cell culture solution or said cell extract, respectively. When the test sample is a protein, it can be contacted with the MK by, for example, introducing a vector of the DNA encoding said protein into a MK expressing cell, or by adding said vector to a cell extract in which the MK is expressed. It is also possible to employ, for example, the two-hybrid method utilizing yeast cells, animal cells, etc.

In the first embodiment, then, the bond between MK and the test compound is detected. There is no particular limitation to the method of detection. The bond between MK and the test compound may, for example, be detected by labels (quantitatively assayable labels, e.g., radiolabels and fluorescent labels) conjugated to the test compound. A labeling agent may also be conjugated to MK. The Bond can also be detected by fixing the test compound or MK to resin or a chip. Furthermore, the bond can be detected using the index of the change in MK activity resulting from the binding of the test compound to MK.

In this embodiment, then, the test compound bound to MK is selected. The selected compound contains a compound that reduces MK expression or activity. Through the inhibition of MK expression or activity, the selected compound may have the effect of increasing in number of regulatory T cells and/or promoting the function of regulatory T cells, and the effect of treating or preventing diseases associated with the functional disorder of regulatory T cells.

In the second embodiment of the screening method of the present invention, the test compound is contacted with MK expressing cells.

In the second embodiment, then, the level of MK expression is assayed. The level of MK expression can be assayed by methods known well to a person skilled in the art. For example, the mRNA of said gene can be extracted in the usual manner, and the transcription level of said gene can be assayed by the Northern hybridization method or RT-PCR method using the mRNA as the template. Furthermore, the level of expression of said gene could be assayed by employing DNA array technology.

The level of gene translation can also be assayed by collecting the fraction containing MK encoded by said gene, and detecting the expression of said MK by means of electrophoresis such as SDS-PAGE. It is also possible to assay the level of gene translation by the Western blotting method using antibodies against MK. Antibodies against MK described above can be used for the method.

In the second embodiment, then, a test compound which reduces MK expression level compared to the MK expression level without the test compound is selected. The selected compound contains a compound that reduces MK expression. Through the inhibition of MK expression, the selected compound may have the effect of increasing the number of regulatory T cells and/or promoting the function of regulatory T cells and the effect of treating or preventing diseases associated with the functional disorder of regulatory T cells.

The third embodiment of the screening method in the present invention provides a cell or cell extract having DNA comprising a reporter gene functionally coupled to the downstream of the promoter region of MK DNA.

In the third embodiment, the expression "functionally coupled" refers to the coupling of the reporter gene to the promoter region of the MK gene so that the expression of the reporter gene may be induced through binding of the transcription factor to the promoter region of the MK gene. Binding the reporter gene can be coupled to another gene to form a fused protein with the other gene product. The coupled gene may also be included in the above-mentioned reporter gene "functionally coupled" the promoter region of the MK. As long as the expression of said fused protein is induced by binding of the transcription factor to the promoter region of the MK gene.

There is no particular limitation to the above-mentioned reporter gene, as long as its expression is detectable. For example, they include, but are not limited to, the CAT gene, lacZ gene, luciferase gene, beta-glucuronidase gene (GUS) and GFP gene, which are commonly used by those skilled in the art. The above-mentioned reporter gene includes DNA that encodes MK.

Cells or cell extracts having DNA comprising a reporter gene functionally coupled to the downstream of the promoter region of MK DNA can be prepared by the method set forth in the first embodiment.

In the third embodiment, then, the test sample is contacted with the above-mentioned cells or cell extract. Then, the level of the above-mentioned reporter gene expression in said cells or cell extract is assayed.

The level of reporter gene expression can be assayed in accordance with the type of reporter gene used by methods known well to a person skilled in the art. For example, when the reporter gene is a CAT gene, the level of reporter gene expression can be assayed by detecting the acetylation of chloramphenicol by said gene product. When the reporter gene is a lacZ gene, the level of reporter gene expression can be assayed by detecting the chromogenicity of the pigment compound caused by the catalytic effect of said gene expression product. When the reporter gene is a luciferase gene, the level of reporter gene expression can be assayed by detecting the fluorescence of the fluorescent compound caused by the catalytic effect of said gene expression product. When the reporter gene is a β-glucuronidase gene (GUS), the level of reporter gene expression can be assayed by detecting the emission of Glucuron (ICN) or the coloring of 5-bromo-4-chloro-3-indolyl-beta-glucuronide(X-Gluc) caused by the catalytic effect of said gene expression product. When the reporter gene is a GFP gene, the level of reporter gene expression can be assayed by detecting the fluorescence of the GFP protein.

When the MK gene is used as the reporter gene, the expression level of said gene can be assayed by the method set forth in the second embodiment.

In the third embodiment, then, a test compound which decreases or increases the expression level of said reporter gene compared to that without the test compound is selected. The selected compound contains a compound that reduces MK expression. Through the inhibition of MK expression, the selected compound may have the effect of increasing the number of regulatory T cells and/or promoting the function of regulatory T cells and the effect of treating or preventing diseases associated with the functional disorder of regulatory T cells.

In the fourth embodiment of the screening method in the present invention, first, a test compound is contacted with the cells that express the MK gene.

In the fourth embodiment, then, the activity of said MK is assayed. MK activity includes promotion of cell proliferation (promotion of fibroblast, keratinocyte or tumor cell proliferation), enhancement of cell survival (enhancement of survival of fetal neurons or tumor cells), promotion of cell migration (promotion of neuron, neutrophil, macrophage, osteoblast or vascular smooth myocyte migration), promotion of chemokine expression, promotion of angiogenesis and promotion of synapse formation. Practically, MK activity can be assayed indirectly by assaying neutrophil and/or macrophage migration capacity or fibroblast proliferation capacity. Then, test compounds which decreases or increases the activity compared to that without the test compound are selected. The selected compound contains a compound that reduces MK activity. Through the inhibition of MK activity, the selected compound has the effect of increasing the number of regulatory T cells and/or promoting the function of regulatory T cells and the effect of treating or preventing diseases associated with the functional disorder of regulatory T cells.

The present invention pertains to a method for treating or preventing diseases associated with the functional disorder of regulatory T cells, including steps of inhibiting MK expression or activity in cells that express MK. In the method of the present invention, the number of regulatory T cells may be increased or the number of type 1 helper T cells may be reduced by inhibiting MK expression or activity.

In the present invention, methods for inhibiting MK expression or activity include administration of RNA that is complementary to the transcription product of DNA encoding MK, or administration of ribozymes that specifically cleave said transcription product to subjects. DNA that encodes MK includes: DNA that comprises the base sequence set forth in SEQ ID NO.: 1; DNA that encodes the protein that comprises the amino acid sequence set forth in SEQ ID NO.: 2; and naturally derived DNA that encodes the protein that comprises the amino acid sequence set forth in SEQ ID NO.: 2 wherein one or a plurality of amino acids in the amino acid sequence has been substituted, deleted, added and/or inserted.

The expression "inhibit MK expression" in the present invention includes the inhibition of gene transcription as well as the inhibition of translation into a protein. It also includes not only the complete termination of DNA expression, but also the reduction of its expression.

When using the MK inhibitor of the present invention as a drug for humans or other animals, it is possible to administer these compounds directly to patients or to administer them after formulation by using well known pharmacological methods. The above-mentioned pharmacologically acceptable excipients may be added for formulation purposes.

All agents of the present invention can be administered in the form of a drug, either systemically (orally or non-orally), or locally. Administration routes include intravenous injection such as intravenous drip, intramuscular injection, intraperitoneal injection, subcutaneous injection, suppository, enema and oral enteric coating drug. The administration route can be selected appropriately depending on the age and symptoms of the patient. The effective dosage is selected from the range of 0.001 mg to 100 mg per kg of body weight. Alternatively, a dosage of 0.1 to 1000 mg, preferably 0.1 to 50 mg per patient can be selected. For example, when the agent is anti-MK antibodies or anti-MK receptor antibodies, the preferable dosage is the effective dosage level that the free antibodies are found in the blood. Specifically, for example, the preferable dosage and administration is a dose of 0.5 mg to 40 mg, preferably 1 mg to 20 mg per kg of body weight per month (4 weeks), either in a single dosage or divided into several dosages, e.g., twice weekly, once weekly, once biweekly, or once every four weeks, by intravenous injection such as intravenous drip, or subcutaneous injection. The administration schedule may be adjusted so that the administration intervals are extended, e.g., once or twice weekly to once biweekly, to once every three weeks, to once every four weeks, while observing the post-administration condition of the patient as well as blood test level behavior. When the agent is an MK aptamer, the effective dosage level is that the free aptamers are found in the blood. Specifically, for example, the preferable dosage and administration is a dose of 0.1 mg to 100 mg, preferably 0.1 mg to 40 mg per kg of body weight per month (4 weeks), either in a single dose or divided into several doses, e.g., twice weekly, once weekly, once biweekly, or once every four weeks, by intravenous injection such as intravenous drip, or subcutaneous injection.

The present invention pertains to a method for examining disease associated with the functional disorder of regulatory T cells. For example, said method include a method for examining disease associated with the functional disorder of regulatory T cells comprising a step of assaying the MK expression level in cells that express MK. The MK expression level can be assayed by methods described above.

When the level of MK expression rises, the number of type 1 helper T cells may be increased (the number of CD25-positive regulatory T cells is decreased). It is believed to be possible to determine the onset of disease associated with the functional disorder of regulatory T cells by assaying the level of MK expression.

The present invention pertains to an agent for examining disease associated with the functional disorder of regulatory T cells.

"Substances that bind with MK" in said agent for examining disease are not limited as long as it binds to MK protein, MK gene region, and/or MK mRNA, and for example, include oligonucleotides that hybridize with the MK gene region and antibodies that recognize MK. Such oligonucleotides that hybridize with the MK gene region include, for example, oligonucleotides having strands comprising of at least 15 nucleotides.

Oligonucleotides used as the agent for examining disease in the present invention include polynucleotides. The oligonucleotides of the present invention may be used as a probe or primer used for detecting or amplifying the DNA encoding MK, a probe or primer used for detecting MK gene expression, or a nucleotide or nucleotide derivative used for inhibiting MK protein expression (e.g., antisense oligonucleotides or ribozymes, or DNA that encodes said antisense oligonucleotides or ribozymes). The oligonucleotides in the present invention may be used in the form of a DNA array substrate.

When using said oligonucleotide as a primer, its length is usually 15 by to 100 bp, preferably 15 by to 30 bp. The primer is not limited as long as it is capable of amplifying the DNA of the present invention or at least part of a complementary strand thereto. Furthermore, when using it as a primer, the 3' region can be a complementary region and a restriction enzyme-recognizing sequence or a tag can be attached to the 5' end.

When using said oligonucleotide as a probe, the probe is not limited as long as it specifically hybridizes with the DNA of the present invention or at least a part of its complementary strand. Said probe may be a synthetic oligonucleotide, and usually has a strand length of at least 15 bp.

When using said oligonucleotide as a probe, it is preferable that the probe is labeled appropriately. Labeling methods include: labeling by phosphorylating the 5' end of the oligonucleotide with $^{32}$P using T4 polynucleotide kinase; and the random prime method, wherein a substrate base labeled by an isotope such as $^{32}$P, fluorescent pigment, biotin, etc. is incorporated into the oligonucleotide using DNA polymerase such as Klenow DNA polymerase with a primer such as random hexamer oligonucleotide.

The oligonucleotide of the present invention can be produced, for example, by a commercially available oligonucleotide synthesizer. The probe can also be produced as a double-stranded DNA fragment obtained by treatment with a restriction enzyme, etc.

The antibodies used as the test agent of the present invention are not limited as long as they recognize the above-mentioned MK, but preferably include those specifically recognize MK. Examples of anti-MK antibodies are listed above.

Antibodies used in the present invention may be conjugated antibodies that are coupled to various molecules such as polyethylene glycol (PEG), radioactive substances and toxins. Such conjugated antibodies can be obtained by chemical modification to the obtained antibodies. Methods for modifying antibodies have already been established in this field. The term "antibodies" in the present invention include such conjugated antibodies.

The test agents listed above may contain, in addition to the active ingredients such as oligonucleotides or antibodies, pharmacologically acceptable excipients already described above.

All related art references cited in this specification are hereby incorporated by reference in their entity.

EXAMPLES

Examples of the present invention are explained as follows, however, the present invention is not limited to following examples.

Example 1

Inducement of Experimental Autoimmune Encephalomyelitis in MK-Deficient Mice, and Observation of Clinical Symptoms First, experimental autoimmune encephalomyelitis was induced in MK-deficient mice, and their clinical condition was observed.

Eight- to ten-week-old wild-type and MK-deficient C57BL-6 mice (provided by Dr. Muramatsu, Nagoya University, Japan; Nakamura, E., et al., *Genes Cells* 3: 811-822 (1998)) were inoculated with 300 µg of myelin oligodendrocyte glycoprotein peptide 35-55 (MOG$_{35-55}$) (MEVGWYR-SPFSRVVHLYRNGK) (SEQ ID NO.: 3) that had been emulsified with 500 µg of incomplete Freund's adjuvant containing killed *Mycobacterium tuberculosis*. Then EAE was induced in the mice by administering 300 ng of pertussis toxin dissolved in 200 µL of PBS immediately after sensitization and 48 hours thereafter. The clinical symptoms of the animals were evaluated daily thereafter by the following standards (FIG. 1). Clinical scores were assigned daily to the wild-type mice (n=16) and MK-deficient mice (n=13) to evaluate the clinical symptoms. The clinical scores in FIG. 1 indicated 0: no symptoms; 1: loss of tail tone; 2: unsteady gait; 3: hind limb paralysis; 4: paralysis of four limbs; 5 death. The proportion of all animals was recorded for the first 25 days following inoculation.

The results indicated mitigation of clinical symptoms in MK-deficient mice (FIG. 1). Specifically, there was delayed disease onset and mitigation of severity of disease in MK-deficient mice after inoculation of MOG$_{35-55}$.

Example 2

Examination of Effect of Administration of MK on the Clinical Symptoms of Experimental Autoimmune Encephalomyelitis in MK-Deficient Mice MK-deficient mice in which experimental autoimmune encephalomyelitis had been induced, were treated with MK, and the effect of MK on the clinical symptoms were examined.

MK dissolved to 1 mg/mL was packed in a micro-osmotic pump (Model 1002, Durect Corp., Cupertino, Calif.) and administered intraperitoneally to MK-deficient mice. A total of 200 mg/day of MK was administered to the mice through this micro-osmotic pump, at a rate of 0.25 μL per hour for 14 days, and their clinical symptoms were evaluated using the same method described in example 1 (n=13). PBS alone was administered intraperitoneally to the control group through the micro-osmotic pump.

The results indicated that the effect of mitigating clinical symptoms in MK-deficient mice disappeared (FIG. 1).

Example 3

Pathologic Examination of Individual Mice

The spinal cord was removed from the mice in each of the groups in examples 1 and 2 after the onset of EAE (day 14 after sensitization), fixed in formalin, stained with hematoxylin-eosin by a well known method, and examined pathologically.

The results indicated a reduction of CNS inflammation in MK-deficient mice after $MOG_{35-55}$ inoculation.

Example 4

Analysis of the Dynamics of CD4-Positive T Cells or CD4-Positive, CD25-Positive Regulatory T Cells in Autoimmune Encephalomyelitis Model Animals The role of MK in EAE expression and CD4-positive, CD25-positive regulatory T cell function was investigated by examining the dynamics of CD4-positive, CD25-positive regulatory T cells in said autoimmune encephalomyelitis model animals.

Lymphocytes were isolated from the spleen, mesenteric lymph nodes and popliteal lymph nodes of mice in the wild-type, MK-deficient and MK-dosed groups after EAE onset (12 to 14 days post-inoculation), and the numbers of CD4-positive, CD8-positive cells and CD4-positive, CD25-positive cells were assayed by flow cytometry.

The results indicated that there were no significant differences in the proportion of CD4-positive T cells between the peripheral lymph nodes of $MOG_{35-55}$ inoculated wild-type mice and those of MK-deficient mice (FIG. 2). Meanwhile, there was increased activity of CD4-positive, CD25-positive T cells in the peripheral lymph nodes of MK-deficient mice (FIG. 3).

Next, the CD4-positive T cells were purified (>95% CD4-positive cells) through a magnetic cell sorter (MACS) and cultured in the presence of $MOG_{35-55}$ (20 μg/mL), and the proportion of CD4-positive, CD25-positive T cells was analyzed by flow cytometry. Practically, 1 mg/mL MK or PBS was administered to wild-type mice and MK-deficient mice through the micro-osmotic pump on the first day in the same manner as described in example 2, then 200 μg/mouse of $MOG_{35-55}$ was administered to them on the first day and two days thereafter. The CD4-positive T cells from the splenocytes of the mice at the peak of their clinical symptoms were purified, and said cells ($2 \times 10^5$ cells per well) were cultured in vitro for four days in the presence of $MOG_{35-55}$ (20 μg/mL) and antigen-presenting cells (hereinafter abbreviated APC; splenocytes of normal mice treated with mitomycin C for 30 minutes at 37° C.; $5 \times 10^6$ cells per well). After four days, the expression of CD4-positive, CD25-positive T cells was analyzed by FACS. Furthermore, cDNA from CD4-positive T cells purified through CD4 microbeads was prepared, and analyzed by real-time RT-RCR to determine the FOXP3 mRNA level.

The results indicated that administration of MK to MK-deficient mice inhibited CD4-positive, CD25-positive T cell expression (FIG. 4).

The above results revealed that the mitigation of clinical symptoms in these model animals was associated not with changes in the CD4-positive cells that induce the disease (FIG. 2), but rather with the increase in the CD4-positive, CD25-positive regulatory T cells (FIGS. 3 and 4).

Example 5

Analysis of the Effect of the Addition of MK on the Dynamics of CD4-Positive, CD25-Positive T Cells in MK-Deficient Mice Next, CD4-positive T cells derived from the spleen of MK-deficient mice were stimulated with $MOG_{35-55}$ in the presence of 0, 20 and 100 ng/mL of MK, and the proportion of CD4-positive, CD25-positive T cells and FOXP3 mRNA expression were analyzed in the same manner as described in example 4.

The results revealed that the proportion and expression of CD4-positive, CD25-positive T cells decreased in MK-deficient mice as the concentration of the MK added increased (FIG. 5).

Example 6

Analysis of the Th1/Th2 Balance in MK-Deficient Mice

Since EAE is a disease induced by type 1 helper T cells (Th1), the Th1/Th2 balance in MK-deficient mice and the effect of MK on the Th1/Th2 balance was examined.

Specifically, CD4-positive T cells from the splenocytes of the mice at the peak of their clinical symptoms of EAE were purified, and said cells ($2 \times 10^5$ cells per well) were cultured in vitro for three days in the presence of $MOG_{35-55}$ (20 μg/mL) and APC. The IFN-gamma and IL-4 levels in the culture supernatant were assayed by ELISA.

The results revealed that type 1 helper cells, which induce cellular immunity, are also inhibited in midkine-deficient mice (FIGS. 6a, 6b).

Example 7

In Vitro Analysis of the Effect of the Addition of Anti-MK Antibodies on the Dynamics of CD4-Positive, CD25-Positive T Cells in EAE Model Mice Preparation of Murine Anti-Human MK Monoclonal Antibodies
(Preparation of MK Gene Knockout Mice)

MK gene knockout mice were produced by well known methods (Japanese published unexamined patent application number 2002-85058; Nakamura, E. et al., Genes Cells 3: 811-822).

(Antigen Preparation)

Human MK mRNA was prepared from Wilms' tumor-derived cultivated cell strain G-401 (Tsutsui, J. et al., Biochem. Biophys. Res. Commun. 176: 792-797, 1991). Human MK cDNA having EcoRI-recognizing sites at both ends of the MK-coding region was prepared by 30 cycles (each cycle comprising a temperature change of 93° C. to 37° C. to 72° C.) of PCR (Polymerase Chain Reaction) of using a sense PCR primer: 5'-GCGGAATTCATGCAGCACCGAGGCT-TCCTC-3' (SEQ ID NO.: 4) and antisense PCR primer: 5'-GCGGAATTCCTAGTCCTTTCCCTTCCCTTT-3' (SEQ ID No.: 5), which were designed such that it contains the sequence recognized by restriction enzyme EcoRI (5'-GAATTC-3'), and using human MK mRNA as the template.

A recombinant expression vector was prepared by EcoRI digesting MK cDNA and the expression vector pHIL301 (containing histidine- and neomycin-resistance gene; see Japanese published unexamined patent application number H02-104292 and European patent application laid-open number 0339568) for yeast (*Pichia pastoris* GS115, hereinafter referred to as "*Pichia* yeast GS115"), and coupling them using a ligation kit (Takara Shuzo Co., Ltd.).

The recombinant expression vector prepared as described above was introduced into *Pichia* yeast GS115 (Invitrogen Corporation) using the electroporation method. A plurality of clones having the target MK gene was obtained by culturing *Pichia* yeast GS115 into which the vector had been introduced in a medium not containing histidine but containing G418. The obtained clones were cultured while induced by methanol. The culture supernatant was collected, and secretion of MK was verified by Western blotting analysis using rabbit anti-murine MK polyclonal antibodies.

One of the clones that secreted MK into the culture supernatant by induction was named T3L-50-4P, and this clone was cultured (see Japanese published unexamined patent application number H07-39889). The MK secretion product was collected from the culture supernatant, and purified by ion-exchange chromatography and affinity chromatography using a heparin column, and then high-purity MK was obtained.

(Immunity)

The MK knockout mice were immunized with MK, an antigen. The antigen formulation was prepared by dissolving 10 μg per mouse of the antigen in 0.1 mL of physiological saline to form an antigen solution and mixing the antigen solution with 0.1 mL of FCA to be emulsified, and then administered subcutaneously in the dorsal skin of the mice. The mice were immunized eight times at two-week intervals. For the eighth immunization, the mice were injected 0.1 mL of the antigen solution containing 10 μg of the antigen to the caudal vein.

The blood antibody level was assayed by ELISA using the serum collected from the ocular fundus of the mice on the sixth day after the fourth immunization and on the eighth day after the sixth immunization.

The ELISA method was implemented as follows. First, the antigen solution was prepared to a concentration of 1.0 μg/mL with PBS (pH=7.2 to 7.4), and dispensed into a 96-well assay plate (manufactured by Falcon Corp., 353912) at a rate of 50 μL/well, and then the plate was incubated overnight at 4° C. to immobilize the antigen. The immobilized antigen was washed three times with 0.05% Tween-PBS. Then 100 μL of four fold dilution of Block Ace (produced by Dainippon Pharmaceutical Co.) was added into each well, and then the plate was incubated for two hours at 37° C. to block. The blocked wells were washed three times with 0.05% Tween-PBS, and then 50 μL of the culture supernatant was added to each well the plate containing the culture supernatant was incubated for one hour at 37° C., and then washed three times with 0.05% Tween-PBS. 50 μL/well of ten-fold Block Ace dilution of goat anti-murine IgG+IgM HRP conjugate (produced by BioSouce Corp., AMI3704) diluted 10000-fold was added as secondary antibodies, and then let the plate was incubated for one hour at 37° C. After washing three times with 0.05% Tween-PBS, 50 μL of HRP substrate (25 mL of substrate solution (10.206 mg/mL of citric acid hydrate and 36.82 mg/mL of disodium hydrogen phosphate in distilled water), 10 mg of OPD and 5 μL of 30% $H_2O_2$) was added into each well, and the plate was incubated in the dark at room temperature for 20 minutes. The reaction was stopped by adding 50 μL/well of 1 N sulfuric acid, and the absorbance was measured at a wavelength of 492 nm.

The antibody levels were sufficiently high in the ELISA performed on the eighth day after the sixth immunization, so the cells were fused three days after two additional immunizations.

(Cell Fusion)

The mice were held and their chest region was wiped with alcohol-soaked cotton, then blood was collected from their heart using a 2.5 mL syringe and 23G needle. After the blood was collected, the mice were placed in a beaker containing 20 mL of alcohol for disinfection for approximately three minutes. The collected blood was placed in a 1.5 mL tube and incubated for one hour at 37° C., followed by overnight at 4° C., and then centrifuged for 10 minutes at 3000 rpm. The serum was transferred to another 1.5 mL tube; added 0.05% sodium azide, and stored at 4° C.

The epithelium of the mice from which the blood had been collected was peeled using scissors and tweezers. Then, the endothelium was lifted, a slit was made, and the spleen was excised. Five petri dishes had been prepared in advance by dispensing 200 mL of RPMI 1640 SP culture medium in each. The excised spleen was washed five times, once in each of the five petri dishes, successively. After washing, the spleen was placed on a mesh strainer and several cuts were made in the spleen with scissors. The spleen was then strained through the mesh strainer with a glass rod. The strainer was washed with RPMI 1640 SP culture medium, and the splenocytes were collected in 40 mL glass centrifuge tubes. The collected splenocytes were centrifuged for 10 minutes at 1200 rpm, and the supernatant was drawn up into a suction pipette. 40 mL of RPMI 1640 SP culture medium was added into the tube, and the tube was centrifuged for 10 minutes at 1200 rpm. The obtained splenocytes were placed in additional 40 mL of RPMI 1640 SP culture medium and agitated thoroughly. The number of cells was counted using a blood cell counter.

Myeloma cells (P3U1) in the petri dish were collected in a 50 mL centrifuge tube by blowing them in using a pipette. The cells were centrifuged for five minutes at 1000 rpm, the supernatant was removed by a suction pipette, and then 40 mL of RPMI 1640 SP culture medium was added into the tube. The tube was centrifuged for five minutes at 1000 rpm, and 40 mL of RPMI 1640 SP culture medium was added to the obtained myeloma cells and agitated thoroughly. The number of cells was counted using a blood cell counter.

Based on the results of the number of cells obtained as set forth above, the myeloma cells were placed in the 50 mL glass centrifuge tube in which the splenocytes had been stored such that the ratio of the number of splenocytes to the number of myeloma cells would be 5:1. After mixing the cells, they were centrifuged for 10 minutes at 1200 rpm, and the supernatant was drawn up into a suction pipette, which was then tapped. After tapping, 1 mL of PEG (polyethylene glycol) was slowly added over one minute while mixing, and the solution was continued to be mixed for an additional two minutes. After mixing with the PEG, 1 mL of RPMI 1640 SP culture medium, which had been preheated to 37° C. in a water bath, was slowly added over one minute while mixing. This process was repeated three times. Then, 10 mL of RPMI 1640 SP culture medium, which had been preheated to 37° C., was slowly added over three minutes while mixing. After adding the culture medium, the culture fluid was heated for five minutes in a 5% $CO_2$ incubator at 37° C., and then centrifuged for five minutes at 1000 rpm. The supernatant was drawn up into a suction pipette, which was then tapped.

After tapping, (number of plates on which the cells are to be seeded)×10 mL of RPMI 1640 SP, 15% FCS, HAT culture medium was blown onto the cells, and using a series of eight micropipettes (each 100 µL) and exclusive trays, a 96-well plate was seeded with the cells using a yellow tip. The cells were cultured for 7 to 14 days in a 5% $CO_2$ incubator at 37° C., and then the antibody production capacity was screened by ELISA according to the colony growth.

(Selection of Anti-Mk-Positive Antibody-Producing Hybridomas)

Ten days after cell fusion, 12 wells among the 96-well culture plate whose supernatant absorbance found to be significantly higher by ELISA were selected for cloning samples. The number of hybridomas was counted, and the hybridomas were seeded on a 96-well culture plate so that three rows had 5 cells/well, three rows had 1 cell/well, and two rows had 0.5 cells/well. Furthermore, $1 \times 10^6$ cells of feeder cells were seeded on each well. Colonies were counted five days after cloning, and wells having single colonies were verified. The culture medium was replaced every two to three days, and when a colony grown to cover one-third of a well, wells indicating a positive reaction by a single colony were selected by ELISA, and the cells which was obtained from the wells wherein a single colony was found to have a positive reaction by ELISA, and which was in a good condition, was established as IP-13.

Next, the anti-MK antibody (IP-13) obtained by the method set forth above was examined for possible inhibitory activity to the MK which inhibit the increase in number of CD4-positive, CD25-positive T cells, using the same method employed in example 4. CD4-positive T cells were isolated from wild-type murine spleens, and cultured in the presence of IP-13 (30 µg/mL), $MOG_{35-55}$ (30 µg/mL) and APC. After five days cultivation, the proportion of CD4-positive, CD25-positive T cells among the CD4-positive T cells was assayed using a flow cytometer. An experiment in which IgG was used instead of IP-13 antibodies was conducted concurrently as a control.

The results revealed that while the proportion of CD4-positive, CD25-positive T cells was 2% in the control experiment, the proportion of CD4-positive, CD25-positive T cells had increased to 4% in the experiment in which IP-13 had been added. These results indicated that the activity of MK to inhibit the increase in number of CD4-positive, CD25-positive cells can be inhibited by using anti-MK antibodies (FIG. 7).

Example 8

Observation of Changes in Clinical Symptoms in EAE Model Mice Resulting from the Addition of Anti-MK Antibodies Anti-MK antibodies were administered to wild-type mice exhibiting clinical symptoms in which experimental autoimmune encephalomyelitis (EAE) had been induced by the method set forth in example 1, and their clinical symptoms were observed.

First, $MOG_{35-55}$ was administered to wild-type EAE model mice (C57BL-6, female, eight weeks old), and then anti-MK antibody (IP14) was administered to the mice on days 0, 3, 7, 10, 14, 17, 21 and 24 (a total of eight dosage) after the administration of $MOG_{35-55}$. The mice were divided into four groups (five mice per group), and the each group was treated with 75 mg/kg body weight, 7.5 mg/kg body weight, 0.75 mg/kg body weight or 0 mg/kg body weight (control) of anti-MK antibodies through the caudal vein. Clinical scores (0: no symptoms; 1: loss of tail tone; 2: laying face up, unable to rise; 3: unstable gait; 4: slight hind limb paralysis; 5: severe hind limb paralysis; 6: death, were assigned daily to evaluate the clinical symptoms.

The results indicated mitigation of clinical symptoms in the groups of mice with administration of anti-MK antibodies (FIG. 8). Specifically, the groups of mice with administration of anti-MK antibodies after being inoculated with $MOG_{35-55}$ exhibited delayed disease onset and mitigation of severity of disease.

Example 9

Experiment of Disease Onset Inhibition in EAE Model Mice Using MK Aptamers

MK aptamers were administered to wild-type mice in which experimental autoimmune encephalomyelitis (EAE) had been induced by the method set forth in example 1, and the inhibitory effect on EAE onset in the mice was observed.

Aptamers that specifically bind to MK were produced using the SELEX method. One of the obtained aptamers was shortened to a length that could be chemically synthesized. In addition, aptamer A, in which nuclease resistance had been enhanced through chemical modification was obtained.

Inhibitory activity of aptamer A to human MK cell migration activity was examined using UMR106 cells (ATCC No. CRL1661), which are rat osteoblast precursor cells. The external surface of chemotaxicell membrane (membrane pore size 8 µm, produced by Kurabo Industries Ltd.) was coated with 30 µL of 1.5 µM MK to immobilize the MK on the external surface of the membrane. The chemotaxicells on which MK had been immobilized were placed on a 24-well culture plate containing 500₄ of culture medium (0.3% bovine serum albumin added, Dulbecco's Modified Eagle's Medium) containing 500 nM aptamer. 200 µL of UMR106 cells were placed in the internal lamina of the chemotaxicell chamber at a concentration of $1 \times 10^6$ cells/mL, and cultured for four hours at 37° C. The residual cells in the internal lamina of the chemotaxicell chamber were removed, and the cells that had penetrated into and adhered to the MK-coated surface were fixed with methanol. The chemotaxicell chamber was immersed in a 1% aqueous crystal violet solution for 30 minutes to stain the cells. The chemotaxicell chamber was washed with distilled water and dried, and then the pigment was extracted with 200₄, of a mixture of 1% SDS and 1% triton×100. 150 µL of the extract was transferred to a 96-well microplate, and the absorbance at 590 nm was measured. The results revealed that aptamer A has strong cell migration-inhibiting activity. If the number of cells that had migrated when no aptamer had been added was set at 100, the number of cells that had migrated when aptamer A had been added was approximately 2.3, hence, a 98% inhibitory activity was verified. Meanwhile, the RNA used as the control indicated no inhibitory activity.

It was examined whether aptamer A plays a role in the increase in number of CD4-positive, CD25-positive regulatory T cells. The experiment was conducted in the same manner as described in example 7. CD4-positive T cells were isolated from the spleens of C57BL-6 mice exhibiting clinical symptoms of EAE in the fourth week after treating with MOG, and said cells ($2 \times 10^5$ cells/well) were cultured in vitro in the presence of MOG$_{35-55}$ (20 μg/mL) and APC for three days after addition of aptamer A. CD4-positive, CD25-positive cell expression was analyzed by FACS. Furthermore, intracellular FOXP3 was detected by flow cytometry, by simultaneously staining CD4-positive cells using the anti-mouse FOXP3 staining set (manufactured by e-Bioscience Corp.). The results of the experiment indicated that the presence proportion of CD4-positive, CD25-positive regulatory T cells was 6.2% in the system in which PBS had been added as the control, while the presence proportion of CD4-positive, CD-25-positive regulatory T cells was 11% in the system in which 125 nM of aptamer A had been added, indicating that the addition of aptamers increases the presence of CD4-positive, CD25-positive regulatory T cells. FOXP3 expression, which is related to the production and differentiation of regulatory T cells, was also investigated. While expression was verified in 25% of the CD4-positive cells in the system in which PBS had been added as the control, expression was increased and verified in 33% of the CD4-positive cells in the system in which 125 nM of aptamer A had been added. These results indicated that the number of CD4-positive, CD25-positive regulatory T cells increases by the addition of aptamer A.

An experiment on inhibition of disease onset in EAE model mice using aptamer A was conducted. Aptamer A was administered intraperitoneally at the dosage of 15 mg/kg of body weight, 2.5 mg/kg of body weight, 0.25 mg/kg or 0 mg/kg of body weight (control), for a total of 10 doses every other day from the day of MOG treatment, to EAE model mice, which were eight-week-old mice (C57BL-6, female) treated with MOG. Each group consists of five to six mice. The mice were observed daily, and each mouse was scored for clinical symptoms based on clinical scores (0: no symptoms; 1: loss of tail tone; 2: laying face up, unable to rise; 3: unstable gait; 4: slight hind limb paralysis; 5: severe hind limb paralysis; 6: death). The results indicated that p<0.01 for the 15 mg/kg group compared to the control group on days 15, 16, 17 and 18 after treatment with MOG, which showed a significant difference statistically (FIG. 9). Dunnett's test was used for statistical analysis. The effect of delaying disease onset was observed in the 15 mg/kg and 2.5 mg/kg groups.

These findings indicated that aptamers that specifically bind to MK, which are MK-inhibitors, can be utilized as a therapeutic drug for multiple sclerosis, which is a disease associated with the reduction of CD4-positive, CD25-positive regulatory T cells.

INDUSTRIAL APPLICABILITY

Inhibiting MK expression or activity increases the number of regulatory T cells, hence, the present invention can be utilized as a method for treating or preventing diseases associated with the functional disorder of regulatory T cells, such as multiple sclerosis, by inhibiting MK through administration of an MK inhibitor, etc. In addition, MK inhibitors can be used as a therapeutic or preventive agent for diseases associated with the functional disorder of regulatory T cells. Furthermore, a therapeutic or preventive agent for diseases associated with the functional disorder of regulatory T cells can be obtained by the screening method of the present invention. The diagnostic method of the present invention can be used as a method for diagnosing diseases associated with the functional disorder of regulatory T cells.

The invention claimed is:

1. A method for increasing a number of regulatory CD4-positive, CD25-positive T cells in a subject having multiple sclerosis, said method comprising administering a midkine (MK) inhibitor to a subject having multiple sclerosis to thereby expand said regulatory T cell population in said subject, wherein the MK inhibitor is an antibody that binds to an MK protein comprising the amino acid sequence of SEQ ID NO: 2.

2. A method for the treatment of multiple sclerosis, said method comprising administering a midkine (MK) inhibitor to a subject having multiple sclerosis, wherein the MK inhibitor is an antibody that binds to an MK protein comprising the amino acid sequence of SEQ ID NO: 2.

* * * * *

SEQUENCE LISTING

```
<160> NUMBER OF SEQ ID NOS: 5

<210> SEQ ID NO 1
<211> LENGTH: 562
<212> TYPE: DNA
<213> ORGANISM: Homo sapiens
<220> FEATURE:
<221> NAME/KEY: CDS
<222> LOCATION: (1)..(432)

<400> SEQUENCE: 1 atg cag cac cga ggc ttc ctc ctc ctc acc ctc ctc gcc ctg ctg gcg      48
Met Gln His Arg Gly Phe Leu Leu Leu Thr Leu Leu Ala Leu Leu Ala
1               5                   10                  15 ctc acc tcc gcg gtc gcc aaa aag aaa gat aag gtg aag aag ggc ggc      96
Leu Thr Ser Ala Val Ala Lys Lys Lys Asp Lys Val Lys Lys Gly Gly
            20                  25                  30 ccg ggg agc gag tgc gct gag tgg gcc tgg ggg ccc tgc acc ccc agc     144
Pro Gly Ser Glu Cys Ala Glu Trp Ala Trp Gly Pro Cys Thr Pro Ser
        35                  40                  45 agc aag gat tgc ggc gtg ggt ttc cgc gag ggc acc tgc ggg gcc cag     192
Ser Lys Asp Cys Gly Val Gly Phe Arg Glu Gly Thr Cys Gly Ala Gln
    50                  55                  60 acc cag cgc atc cgg tgc agg gtg ccc tgc aac tgg aag aag gag ttt     240
Thr Gln Arg Ile Arg Cys Arg Val Pro Cys Asn Trp Lys Lys Glu Phe
65                  70                  75                  80 gga gcc gac tgc aag tac aag ttt gag aac tgg ggt gcg tgt gat ggg     288
Gly Ala Asp Cys Lys Tyr Lys Phe Glu Asn Trp Gly Ala Cys Asp Gly
                85                  90                  95
```

-continued

```
ggc aca ggc acc aaa gtc cgc caa ggc acc ctg aag aag gcg cgc tac    336
Gly Thr Gly Thr Lys Val Arg Gln Gly Thr Leu Lys Lys Ala Arg Tyr
            100                 105                 110 aat gct cag tgc cag gag acc atc cgc gtc acc aag ccc tgc acc ccc    384
Asn Ala Gln Cys Gln Glu Thr Ile Arg Val Thr Lys Pro Cys Thr Pro
        115                 120                 125 aag acc aaa gca aag gcc aaa gcc aag aaa ggg aag gga aag gac tag    432
Lys Thr Lys Ala Lys Ala Lys Ala Lys Lys Gly Lys Gly Lys Asp
    130                 135                 140 acgccaagcc tggatgccaa ggagccctg gtgtcacatg gggcctggcc cacgccctcc     492
ctctcccagg cccgagatgt gacccaccag tgccttctgt ctgctcgtta gctttaatca    552
atcatgcccc                                                           562
```

```
<210> SEQ ID NO 2
<211> LENGTH: 143
<212> TYPE: PRT
<213> ORGANISM: Homo sapiens

<400> SEQUENCE: 2

Met Gln His Arg Gly Phe Leu Leu Thr Leu Leu Ala Leu Leu Ala
1               5                   10                  15

Leu Thr Ser Ala Val Ala Lys Lys Lys Asp Lys Val Lys Lys Gly Gly
            20                  25                  30

Pro Gly Ser Glu Cys Ala Glu Trp Ala Trp Gly Pro Cys Thr Pro Ser
        35                  40                  45

Ser Lys Asp Cys Gly Val Gly Phe Arg Glu Gly Thr Cys Gly Ala Gln
    50                  55                  60

Thr Gln Arg Ile Arg Cys Arg Val Pro Cys Asn Trp Lys Lys Glu Phe
65                  70                  75                  80

Gly Ala Asp Cys Lys Tyr Lys Phe Glu Asn Trp Gly Ala Cys Asp Gly
                85                  90                  95

Gly Thr Gly Thr Lys Val Arg Gln Gly Thr Leu Lys Lys Ala Arg Tyr
            100                 105                 110

Asn Ala Gln Cys Gln Glu Thr Ile Arg Val Thr Lys Pro Cys Thr Pro
        115                 120                 125

Lys Thr Lys Ala Lys Ala Lys Ala Lys Lys Gly Lys Gly Lys Asp
    130                 135                 140
```

```
<210> SEQ ID NO 3
<211> LENGTH: 21
<212> TYPE: PRT
<213> ORGANISM: Artificial
<220> FEATURE:
<223> OTHER INFORMATION: Myelin oligodendrocyte glycoprotein peptide
      35-55

<400> SEQUENCE: 3

Met Glu Val Gly Trp Tyr Arg Ser Pro Phe Ser Arg Val Val His Leu
1               5                   10                  15

Tyr Arg Asn Gly Lys
            20
```

```
<210> SEQ ID NO 4
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 4
```

```
gcggaattca tgcagcaccg aggcttcctc                                      30

<210> SEQ ID NO 5
<211> LENGTH: 30
<212> TYPE: DNA
<213> ORGANISM: Artificial
<220> FEATURE:
<223> OTHER INFORMATION: An artificially synthesized primer sequence

<400> SEQUENCE: 5
gcggaattcc tagtcctttc ccttcccttt                                      30
```